US008981073B2

United States Patent
Mori et al.

(10) Patent No.: US 8,981,073 B2
(45) Date of Patent: Mar. 17, 2015

(54) HEPATITIS C VIRUS GENE

(75) Inventors: Kenichi Mori, Wako (JP); Noboru Maki, Wako (JP); Hiromi Fukai, Wako (JP)

(73) Assignee: Advanced Life Science Institute, Inc., Wako-Shi (JP)

( * ) Notice: Subject to any disclaimer, the term of this patent is extended or adjusted under 35 U.S.C. 154(b) by 23 days.

(21) Appl. No.: 13/823,422

(22) PCT Filed: Oct. 7, 2011

(86) PCT No.: PCT/JP2011/073189
§ 371 (c)(1),
(2), (4) Date: Apr. 8, 2013

(87) PCT Pub. No.: WO2012/046836
PCT Pub. Date: Apr. 12, 2012

(65) Prior Publication Data
US 2013/0189779 A1    Jul. 25, 2013

(30) Foreign Application Priority Data

Oct. 8, 2010    (JP) ................................ 2010-228152

(51) Int. Cl.
*C07H 21/04*    (2006.01)
*A01N 63/02*    (2006.01)
*C12N 7/00*    (2006.01)
*C07H 21/02*    (2006.01)
*C07K 14/005*    (2006.01)

(52) U.S. Cl.
CPC .............. *C07H 21/02* (2013.01); *C07K 14/005* (2013.01); *C12N 2770/24222* (2013.01)
USPC .................... 536/23.72; 424/93.21; 424/93.6; 435/235.1

(58) Field of Classification Search
None
See application file for complete search history.

(56) References Cited

U.S. PATENT DOCUMENTS

2010/0173298 A1    7/2010    Mori et al.

FOREIGN PATENT DOCUMENTS

JP    2002-171978 A    6/2002
WO    WO 2008/136470 A1    11/2008

OTHER PUBLICATIONS

Dentzer, "Determinants of the Hepatitis C Virus Nonstructural Protein 2 Protease Domain Required for Production of Infectious Virus," Journal of Virology, vol. 82, No. 24, Dec. 2009, pp. 12702-12713.
Foster et al., "A comparative analysis of the fluorescence properties of the wild-type and active site mutants of the hepatitis C virus autoprotease NS2-3," Biochemica et Biophysica Acta, No. 1804, 2010, pp. 212-222.
International Search Report for International Application No. PCT/JP2011/073189, mailed Dec. 6, 2011, including English translation.
Wakita et al., "Production of infectious hepatitis C virus in tissue culture from a cloned viral genome," Nat. Med., vol. 11, No. 7, Jul. 2005, pp. 791-796.
Welbourn et al., "Hepatitis C Virus NS2/3 Processing is Required for NS3 Stability and Viral RNA Replication," The Journal of Biological Chemistry, vol. 280, No. 33, Aug. 19, 2005, pp. 29604-29611.
Welbourn et al., "Investigation of a role for lysine residues in nonstructural proteins 2 and 2/3 of the hepatitis C virus for their degradation and virus assembly," Journal of General Virology, No. 90, 2009, pp. 1071-1080.
Welbourn et al., "The Hepatitis C Virus NS2/3 Protease," Curr. Issues Mol. Biol., 2007, vol. 9, No. 1, 2007, pp. 63-70.
Yi et al., "Production of infectious genotype 1a hepatitis C virus (Hutchinson strain) in cultured human hepatoma cells," PNAS, Feb. 14, 2006, vol. 103, No. 7, Feb. 14, 2006, pp. 2310-2315.

*Primary Examiner* — Nicole Kinsey White
(74) *Attorney, Agent, or Firm* — Birch, Stewart, Kolasch & Birch, LLP

(57) ABSTRACT

Disclosed are an HCV gene having higher replication efficiency and higher reinfection efficiency than the known HCV gene of genotype 1b, an RNA replicon having this gene, a cell infected with this RNA replicon, which cell allows replication of HCV, and an HCV particle. The hepatitis C virus gene encodes an amino acid sequence wherein the 979th amino acid is threonine; the 1804th amino acid is leucine; and the 1966th amino acid is lysine. An HCV gene which can propagate in vitro and has higher replication efficiency and higher reinfection efficiency than the known HCV gene of genotype 1b was provided.

9 Claims, 3 Drawing Sheets

HEPATITIS C VIRUS GENE

TECHNICAL FIELD

The present invention relates to a hepatitis C virus (which may be hereinafter referred to as "HCV") gene, an RNA replicon containing the gene, a cell infected with the RNA replicon, which cell allows replication of HCV, and an HCV particle.

BACKGROUND ART

HCV is a causal factor of chronic hepatitis C, and, according to statistics reported by WHO, it is assumed that there are 170 million infected patients in the world. HCV is a virus classified into the genus *Flavivirus* in the family Flaviviridae. It is considered that infection with the virus occurs via blood or a blood component, and the virus grows in liver. In the initial phase of infection, patients infected with HCV show only mild symptoms, but the infection becomes chronic at high frequency, leading, after a certain length of asymptomatic period, to development of chronic hepatitis. As the infection continues, exacerbation of the disease condition occurs to cause liver cirrhosis, which then leads to liver cancer at high frequency. It is considered that hepatitis virus is involved in 95% of liver cancer, and that infection with HCV is responsible for 80% of such cases.

For treatment of chronic hepatitis C, interferon is widely used. In recent years, the rate of complete cure by elimination of HCV in vivo has been gradually increasing due to improved formulations of interferon and improved administration methods such as combination therapy with interferon and ribavirin. However, the complete cure rate by administration of interferon is still about 50%, and it is considered that many types of HCV are resistant to interferon therapy. Thus, development of a drug having a therapeutic effect against the interferon-resistant virus has been demanded.

Development of such a drug requires a drug screening system. Although a method by infecting cells derived from human or monkey with HCV in vitro and propagating HCV has been reported, such a propagation system could not be used as a drug screening system because of both low infection efficiency and low growth efficiency.

Wakita et al. isolated an HCV gene of genotype 2a from a fulminant hepatitis C patient (Patent Document 1). From the isolated JFH1 strain, full-length RNA was synthesized in vitro, and the RNA was transfected into human liver cancer-derived cells (Huh7 cells). As a result, a replicon RNA that autonomously replicates in the cells was successfully obtained. Further, release of infectious particles into the culture supernatant of the cells into which the replicon RNA was transfected was confirmed (Non-patent Document 1). Therefore, by transfecting the replicon RNA of the JFH1 strain into human liver cancer-derived cells (Huh7 cells) and culturing the obtained infectious particles again with human liver cancer-derived cells, a reinfection-propagation system can be constructed. By using this reinfection-propagation system, screening of drugs against HCV has been started.

However, the JFH1 strain is HCV of genotype 2a, which is an interferon-sensitive HCV. Therefore, since the strain does not have an HCV gene region responsible for resistance to interferon, host factors that act on the region providing resistance to interferon cannot be identified. Thus, screening of drugs effective against interferon-resistant HCV might be impossible.

Lemon et al. reported an infection-propagation system prepared by transfecting the replicon RNA of the H77 strain of genotype 1a into human liver cancer-derived cells (Huh7 cells) (Non-patent Document 2). However, when virus particles obtained from the culture supernatant of the cells having the transfected replicon RNA were used again for infection of the human liver cancer-derived cells, the infectivity titer was 400 times lower than that of infectious particles of the JFH1 strain. Therefore, it is considered that the replicon RNA of the H77 strain releases virus particles which lost the infectivity. Thus, it is considered that the replicon RNA of the H77 strain which can replicate in vitro has already lost the function to produce infectious particles and does not have the inherent growth function of HCV. Thus, screening of drugs effective against HCV having the function to grow in the living body might be impossible with a screening system using the infection-propagation system of the replicon RNA of the H77 strain.

Although, as described above, the replicon RNAs reported by Wakita and by Lemon partially enabled screening of drugs, those replicon RNAs have the above-described problems, and it is considered that screening of drugs that can be widely used for treatment of HCV is impossible with those replicon RNAs.

Further, for obtaining a drug that can be widely used for treatment of HCV, the present inventors also developed pTPF1/4B as an in vitro propagation system which has an efficient HCV propagation, gene of genotype 1b, resistance to interferon, and ability to produce infectious particles (Patent Document 2). However, this culture system was practically problematic in Huh7 cells, which are human liver cancer-derived cells, since the efficiencies of autonomous replication in the cell, self-replication of RNA and secretion of virus particles into the culture supernatant were poor. Further, in Non-patent Document 3, it is reported that there is a region, in the C-terminus side of the NS2 region, which is important for infectivity.

PRIOR ART DOCUMENTS

Patent Documents

[Patent Document 1] JP 2002-171978 A
[Patent Document 2] WO2008/136470
[Non-patent Document 1] Nature Medicine, 2005, vol. 11, pp. 791-796.
[Non-patent Document 2] Proceeding of the National Academy of Science of the United State of America, 2006, vol. 103, pp. 2310-2315.
[Non-patent Document 3] Journal of Virology, 2009, vol. 83, pp. 12702-12713.

SUMMARY OF THE INVENTION

Problems to be Solved by the Invention

As described above, the present inventors discovered that TPF1/4B replicon RNA, which is an HCV gene derived from a fulminant hepatitis C patient showing resistance to interferon and has two amino acid mutations in the region of NS4B protein, shows high replication efficiency and releases infectious particles into the culture supernatant (Patent Document 2). However, for its application to a high-throughput screening system for more efficient drug search, an improved HCV gene having higher replication efficiency and higher reinfection efficiency needs to be obtained.

Accordingly, the present invention aims to provide an HCV gene having higher replication efficiency and higher reinfection efficiency than the known HCV gene described in Patent Document 2. The present invention also aims to provide an RNA replicon having the gene of the present invention described above, a cell infected with the RNA replicon, which cell allows replication of HCV, and an HCV particle.

Means for Solving the Problems

As a result of intensive study, the present inventors discovered that, by mutating the 170th amino acid in the NS2 region in the gene of the TPF1/4B strain described in Patent Document 2 from Met to Thr, the replication efficiency and the reinfection efficiency can be significantly increased, thereby completing the present invention.

That is, the present invention provides a hepatitis C virus gene that encodes threonine as the 979th amino acid, leucine as the 1804th amino acid and lysine as the 1966th amino acid. The present invention also provides an RNA replicon comprising the gene of the present invention. The present invention also provides a cell infected with the RNA replicon of the present invention, which cell allows replication of hepatitis C virus. The present invention also provides a hepatitis C virus particle having the gene of the present invention.

Effects of the Invention

By the present invention, an HCV gene which is capable of propagating in vitro and has higher replication efficiency and higher reinfection efficiency than the known HCV gene described in Patent Document 2 was provided for the first time. By using the HCV gene of the present invention, in vitro analysis of the HCV genome replicating in vivo is possible. By using this HCV genome, an infected-cell model simulating its replication in the liver of a patient that leads to exacerbation of hepatitis can be constructed. By using this model, development and screening of pharmaceutical agents that suppress/inhibit exacerbation of hepatitis are possible.

BEST MODE FOR CARRYING OUT THE INVENTION

Figure 1:
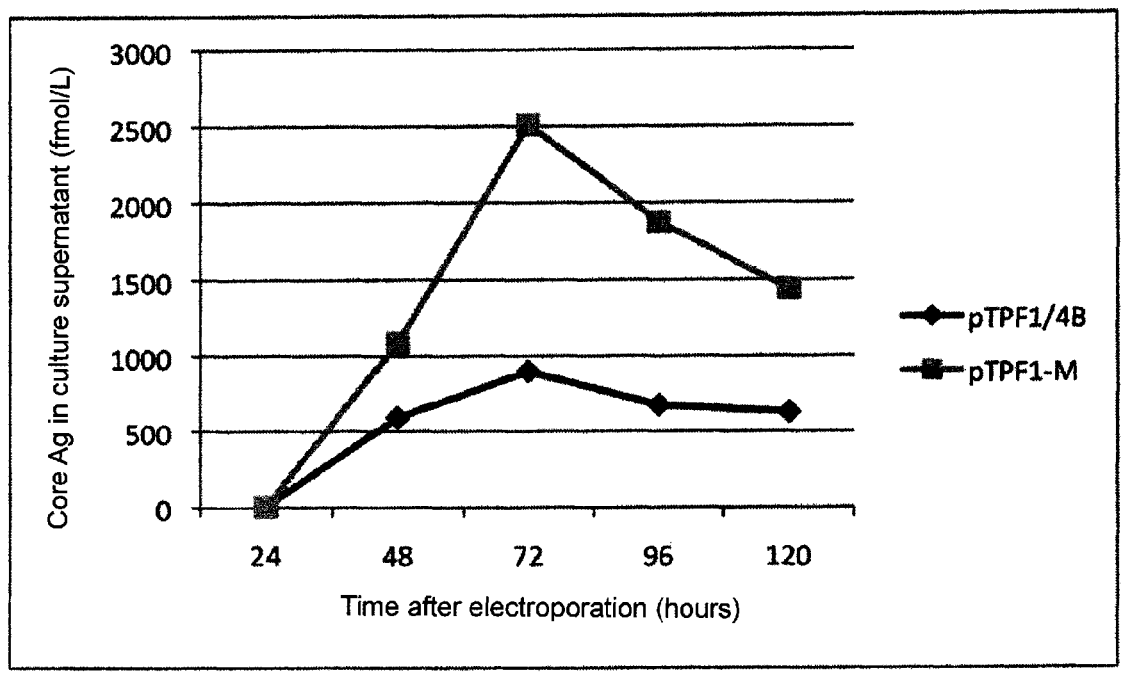
FIG. 1 is a diagram showing the relationship between the time after electroporation by which the RNA replicon having the HCV gene of the present invention (pTPF1-M) prepared in Example below was transfected into cells and the concentration of the core antigen in the culture supernatant, together with the result for the HCV gene described in Patent Document 2 (pTPF1/4B).

As described above, the HCV gene of the present invention is characterized in that the gene encodes threonine as the 979th amino acid, leucine as the 1804th amino acid and lysine as the 1966th amino acid. Among these, the leucine as the 1804th amino acid and the lysine as the 1966th amino acid are characteristics of the gene of the TPF1/4B strain described in Patent Document 2, and these two mutations allow self-replication of HCV in vitro and hence culture of HCV in vitro. The HCV of the present invention has these two mutations characteristic to the TPF1/4B strain, and additionally has a mutation in the NS2 region when compared to the gene of the TPF1/4B strain. That is, the amino acid sequence encoded by the HCV gene has threonine (instead of methionine in the TPF1/4B strain) at position 979 (170th amino acid in the NS2 region). SEQ ID NO:3 shows the nucleotide sequence of only the NS2 region together with the amino acid sequence encoded thereby, and SEQ ID NO:4 shows only the amino acid sequence.

SEQ ID NO:1 shows the nucleotide sequence of the HCV gene obtained in Example below together with the amino acid sequence encoded thereby. SEQ ID NO:2 shows only the amino acid sequence in SEQ ID NO:1. The above-described amino acid positions defined in the present invention are based on the amino acid sequence shown in SEQ ID NO:2, and, since the amino acid sequence shown in SEQ ID NO:2 has the same 3010 amino acids as those in the amino acid sequence of the common 1b-type HCV except for the amino acids at above-described sites having mutations, the positions are the same as those in the amino acid sequence of the common 1b-type HCV. In cases where the number of amino acids is not 3010, the positions of the above-described 3 amino acids defined in the present invention in the amino acid sequence can be easily identified by using well-known software for calculation of the sequence identity (mentioned later) to align the sequence with the amino acid sequence shown in SEQ ID NO:2 such that the number of matched amino acids is maximum. In such cases, the amino acids at the identified sites need to be the above-described 3 amino acids. In the nucleotide sequence shown in SEQ ID NO: 1 and other known 1b-type HCV genes, 5'-UTR corresponds to positions 1 to 341 in the nucleotide sequence; the core corresponds to positions 342 to 914 in the nucleotide sequence; the E 1 region corresponds to positions 915 to 1490 in the nucleotide sequence; the E2 region corresponds to positions 1491 to 2579 in the nucleotide sequence; the P7 region corresponds to positions 2580 to 2768 in the nucleotide sequence; the NS2 region corresponds to positions 2769 to 3419 in the nucleotide sequence; the NS3 region corresponds to positions 3420 to 5312 in the nucleotide sequence; the NS4A region corresponds to positions 5313 to 5474 in the nucleotide sequence; the NS4B region corresponds to positions 5475 to 6257 in the nucleotide sequence; the NS5A region corresponds to positions 6258 to 7598 in the nucleotide sequence; the NS5B region corresponds to positions 7599 to 9371 in the nucleotide sequence; and 3'-untranslated region corresponds to positions 9372 to 9594. Therefore, among the mutation sites in the gene of the present invention, the 1804th amino acid corresponds to the 93rd amino acid in the NS4B region, and the 1966th amino acid corresponds to the 255th amino acid in the NS4B region.

The HCV gene of the present invention includes not only those composed of RNA but also those composed of DNA. In cases of RNA, each "t" in the nucleotide sequences shown in SEQ ID NO:1 and SEQ ID NO:3 is read as "u" instead. Accordingly, within the scope of the present specification and claims, when a nucleotide sequence is mentioned, the nucleotide sequence shown by SEQ ID NO is interpreted to also include the nucleotide sequence having u instead of t.

As is evident from the fact that various variants are known for the HCV gene, even a nucleotide sequence having a small number of mutations when compared with the nucleotide sequence shown in SEQ ID NO:1 can constitute hepatitis C virus having replication capacity and infection ability, and a gene which encodes an amino acid sequence having the above-described 3 amino acids and constituting hepatitis C virus having replication capacity and infection ability is also included within the scope of the present invention. That is, a gene which encodes an amino acid sequence having a sequence identity of not less than 95%, preferably not less than 99% with the amino acid sequence shown in SEQ ID NO:2 and constituting hepatitis C virus having replication capacity and infection ability (provided that the 979th amino acid is threonine; 1804th amino acid is leucine; and 1966th amino acid is lysine) is included within the scope of the present invention. The sequence identity herein means a value determined by aligning two amino acid sequences such that the number of matched amino acid residues is maximum (by inserting a gap(s) as required) and dividing the number of matched amino acid residues by the number of amino acid residues in the full-length sequence (in cases where the two sequences have different total numbers of amino acid residues, amino acid residues in the longer sequence). Such calculation of the sequence identity can be easily carried out using well-known software such as genetic analysis software including BLAST and MacVector (Version 10.5.1, MacVector). In cases where the gene is used for thug-discovery screening, the HCV is preferably as close to naturally occurring HCVs as possible. Therefore, mutations other than the 3 amino acid mutations characteristic to the present invention are preferably those found in naturally occurring HCVs. Further, the nucleotide sequence is preferably the nucleotide sequence shown in SEQ ID NO:1 (wherein t may instead be u) or a sequence having a sequence identity of not less than 90%, more preferably not less than 95%, still more preferably not less than 99% therewith. Whether or not the virus has replication capacity and infection ability can be judged by infecting a hepatic cell strain such as Huh7 cells with the virus and seeing if HCV can be detected in the culture supernatant of the cells, and a specific method is described in Example below.

The HCV gene having the nucleotide sequence shown in SEQ ID NO:1 is the 1b type. Since the 1b type shows interferon resistance, it is important as a subject of drug-discovery screening. Thus, the HCV gene of the present invention is preferably the 1b type. Genotypes of HCV have been well studied, and methods of genotyping are described in literatures such as Okamoto et al. (Virology, 1992, vol. 188, pp. 331-341) and Simmonds et al. (Journal of General Virology, 1993, vol. 74, pp. 2391-2399). Those skilled in the art can easily carry out genotyping of HCV.

The HCV gene of the present invention can be prepared by introducing a mutation(s) into a known HCV gene, preferably the known 1b-type HCV gene, by a method such as the well-known site-directed mutagenesis, such that the amino acid sequence encoded by the gene has the above-described 3 amino acids. Since, as described above, the TPF1/4B strain described in Patent Document 2 has the two mutations in the NS4B region, in cases where the TPF1/4B strain is used as the starting gene, the HCV gene of the present invention can be prepared by introducing one mutation into the NS2 region. Since the method of site-directed mutagenesis is well known and kits therefor are commercially available, this can be easily carried out. The introduction of mutation can be carried out by, for example, performing PCR (PCR Protocols, Academic Press (1990)) using specific primers to introduce the amino acid substitution to the NS2 region (see Example below). The gene may be cloned into, for example, pGEM-T easy vector (manufactured by Promega), and its nucleotide sequence may be determined with an automatic sequencer. Further, by digesting the HCV gene having the amino acid substitution with restriction enzymes AgeI and FseI and ligating the resulting fragment to pTPF1/4B similarly digested with the restriction enzymes, the full-length HCV gene of the present invention having the mutation in the NS2 region can be obtained (see Example below). In cases where another type of HCV gene is used as the starting gene, additional two mutations need to be introduced into the NS4B region, and the introduction can be easily carried out similarly by site-directed mutagenesis or the like. The HCV gene can be obtained by recovering HCV particles from blood of a hepatitis patient and extracting RNA by a conventional method.

The replicon RNA (also called RNA replicon) of the present invention having the HCV gene of the present invention described above can be prepared using an arbitrary genetic engineering technique. The replicon RNA can be prepared by, for example, the following method, although the method of preparation is not restricted.

The DNA encoding a replicon RNA is inserted into a cloning vector by a conventional method, to prepare a DNA clone. This DNA is inserted into the downstream of an RNA promoter, to prepare a DNA clone that can construct the replicon RNA. The RNA promoter is preferably contained in a plasmid clone. Examples of the RNA promoter include, but are not limited to, T7 RNA promoter, SP6 RNA promoter and SP3 RNA promoter, and the RNA promoter is especially preferably T7 RNA promoter.

The vector into which the DNA is to be inserted is not restricted, and examples of the vector include plasmid vectors; linear double-stranded DNA vectors; and virus vectors such as adenovirus vectors, adeno-associated virus vectors, retrovirus vectors and lentivirus vectors. The vector is preferably a plasmid vector.

The replicon RNA of the present invention can be prepared from the vector into which the DNA was inserted. Using the DNA clone as a template, RNA is synthesized with RNA polymerase. The RNA synthesis can be started from the 5'-untranslated region by a conventional method. In cases where the template DNA is a plasmid clone, the DNA region linked to the downstream of an RNA promoter may be cleaved out with a restriction enzyme(s), and the obtained DNA fragment may be used as a template to synthesize RNA. The 3'-end of the synthesized RNA is preferably the same as the 3'-untranslated region of the virus genome RNA, with neither addition nor deletion of another sequence thereto. For example, in a preferred mode of the full-length replicon RNA of the present invention, the DNA is inserted into a vector having a T7 RNA promoter upstream of the 5'-UTR and a XbaI restriction site at the end of 3'-UTR. The resulting vector is digested with XbaI, and the HCV genomic RNA can then be synthesized with T7 RNA polymerase.

The replicon-replicating cell of the present invention can be prepared by transfecting the RNA replicon into an arbitrary cell. The cell into which the replicon RNA is to be transfected is not restricted, and the cell is preferably a human liver-derived cell, mouse liver-derived cell or monkey liver-derived cell, especially preferably Huh7 cell, HepG2 cell or Hep3B cell, which are human liver cancer-derived cells, or IMY-N9 cell, HeLa cell, CHO cell, COS cell, Vero cell or 293 cell. The human liver cancer-derived cells Huh7 cell, HepG2 cell and Hep3B cell are especially preferred. By subjecting these cells, preferably human liver cancer-derived cells, to limiting dilution to obtain monoclonal cells, and transfecting the replicon RNA to the obtained cells, a large amount of the replicon RNA can be produced, which is preferred. For example, as concretely described in Example below, when the RNA replicon was transfected into ALS32 cells, which are monoclonal cells established by subjecting human liver cancer-derived Huh7 cells to limiting dilution (medium: D-MEM medium supplemented with 10% FBS), a much larger amount of the replicon RNA was produced than in the case where the RNA replicon was transfected into their parent cells, Huh7 cells. The replicon RNA can be transfected into the cells by an arbitrary transfection method. Examples of such a transfection method include electroporation, particle gun method and lipofection. Among these, the method by electroporation is especially preferred.

In cases where a replicon RNA containing a selection marker gene or reporter gene is used in the transfection into cells, cells into which the replicon RNA was transfected and in which the replicon RNA is continuously replicating can be selected utilizing expression of the selection marker gene or reporter gene. For example, in cases where the replicon RNA contains a neomycin-resistance gene as a selection marker gene, the cells after transfection with the replicon RNA are plated in a culture dish, and G418 (neomycin) is added thereto at a concentration of 0.05 mg/ml to 3.0 mg/ml. Thereafter, the culture is continued while the culture medium is replaced twice a week. The cells become visible as colonies 2 or 3 weeks after the plating.

The replicon-replicating cell of the present invention produces replicon RNA, hepatitis C virus protein and hepatitis C virus particles. Therefore, the replicon-replicating cell can be used for producing replicon RNA, hepatitis C virus protein and hepatitis C virus particles.

The replicon RNA replicated in the replicon-replicating cell can be extracted from the cell by an arbitrary RNA extraction method. The RNA extracted from the cell can be made to function as the replicon RNA again by transfection into the cell. The cell which may be used in this case is Huh7 cell, HepG2 cell or Hep3B cell, which are human liver cancer-derived cells, or IMY-N9 cell, HeLa cell, CHO cell, COS cell, Vero cell or 293 cell; more preferably Huh7 cell, HepG2 cell or Hep3B cell, which are human liver cancer-derived cell; especially preferably a monoclonal cell obtained by subjecting these human liver cancer-derived cells to limiting dilution, which monoclonal cell has improved replication capacity of the replicon RNA compared to its parent cell (e.g., ALS32 cell described in Example). As the hepatitis C virus protein of the present invention, either the protein in the cell or the protein secreted into the culture supernatant may be used. The produced hepatitis C virus protein can be extracted and purified by known methods. As the hepatitis C virus particles produced by the replicon-replicating cell, either the particles in the cell or the particles secreted into the culture supernatant may be used. The replicon RNA may be altered to modify the hepatitis C virus protein and hepatitis C virus particles of the present invention, in order to reduce the pathogenicity by modification of the RNA, virus protein or virus particles for use as a vaccine.

By using the replicon-replicating cell, screening of substances that control infection with hepatitis C virus can be carried out. The term "control infection with hepatitis C virus" means, for example, regulation (e.g., promotion or suppression) of replication of HCV RNA or regulation (e.g., promotion or suppression) of translation from RNA into protein.

More specifically, screening of a test substance can be carried out by bringing the test substance into contact with the replicon-replicating cells and analyzing the degree of increase in the replicon RNA. The degree of increase in the replicon RNA means the amount of change in the replication rate or in the amount of replicon RNA. More specifically, screening of a test substance can be carried out by detecting or measuring the amount of replicon RNA in the replicon cells or in the supernatant, and comparing the measured value with the amount of replicon RNA in control replicon-replicating cells that were not brought into contact with the test substance. The screening of a test substance can also be carried out by detecting or measuring the amount of hepatitis C virus protein in the cells or in the supernatant, and comparing the measured value with that of replicon-replicating cells that were not brought into contact with the test substance. The hepatitis C virus protein which can be detected or measured in the screening is not restricted, and the protein is preferably the core protein. The core protein may also be measured using a commercially available kit. Further, automation of the screening method may be applied to a high-throughput screening process.

Further, the screening method of the present invention is also effective as a method for evaluation of an effect of a screened drug. In cases where evaluation of a drug needs to be carried out by this screening method, the method can also be used as a method for producing the drug.

The present invention is concretely described below by way of Example. However, the present invention is not limited to the Example below.

REFERENCE EXAMPLE

Obtaining TPF1/4B Strain Gene

By the method described in Examples in Patent Document 2, the TPF1/4B strain gene was obtained and analyzed. That is, the following operation was carried out.

(A) Extraction of RNA from Serum

From 250 μL of serum collected from a fulminant hepatitis patient in the acute stage, RNA was purified using the High Pure Viral Nucleic Acid Kit (Roche diagnostics corporation) according to the method recommended by the manufacturer.

(B) Synthesis of cDNA, and Amplification of cDNA by PCR

To the purified RNA, the XR58R primer was added, and reverse transcription was performed with SuperSucript II reverse transcriptase (Invitrogen) according to the method recommended by the manufacturer at 42° C. for 1 hour, to obtain cDNA. To the obtained reaction solution, RNase H (Invitrogen) was added, and the reaction was allowed to proceed at 37° C. for 30 minutes to degrade RNA. The resulting reaction solution was subjected to polymerase chain reaction (PCR) using the HC-LongA1 primer, 1b9405R primer and Takara LA Taq DNA polymerase (Takara Shuzo Co., Ltd.)

wherein thermal cycling reaction was performed by 30 cycles of 94° C. for 20 seconds and 68° C. for 9 minutes, to amplify the cDNA. Further, a part of the obtained reaction solution was subjected to PCR using the HC85F and HC9302R primers, to amplify HCV cDNA.

(C) Cloning of cDNA

The amplified DNA fragment was separated by electrophoresis using 0.7% agarose gel, and recovered using the QIAquick gel purification kit (QIAGEN) according to the method recommended by the manufacturer. The recovered DNA fragment was subjected to ligation reaction with pGEM-T easy vector (Promega), and the resulting plasmid was used for transformation of the DH5α strain. An ampicillin-resistant transformant was selected and cultured using 2YT medium. From the cultured bacterial cells, plasmid was purified using Wizard Plus SV Miniprep DNA Purification System.

(D) Determination of Nucleotide Sequence

The nucleotide sequence of HCV cDNA was determined using primers (SEQ ID NOs:17 to 39) designed based on the nucleotide sequence of HCV of genotype 1b. Using the CEQ DTCS Quick Start Kit (Beckman Coulter) according to the method recommended by the manufacturer, the reaction was performed, and analysis was carried out by the CEQ2000 XL DNA analysis system (Software version 4.0.0, Beckman Coulter). The obtained data were analyzed with Sequencher (Version 4.1.2, Gene Codes Corporation). The obtained HCV clone was designated pTPF1-0193.

(E) Obtaining cDNA of 5'-Untranslated Region and Determining Its Nucleotide Sequence Further, the RNA obtained in the above Step (A) was subjected to 5'-RACE to obtain cDNA at the end of the 5'-untranslated region. The reaction was performed using 5'-RACE System for Rapid Amplification of cDNA Ends, Version 2.0 (Invitrogen) according to the instruction provided by the manufacturer.

As an antisense primer for cDNA synthesis, Chiba-as was used. cDNA was synthesized with SuperScript II Reverse Transcriptase (Invitrogen) and purified with S.N.A.P column, followed by subjecting the purified cDNA to TdT-tailing reaction to add dCTPs. Using the 5'RACE Abridged Anchor primer attached to the kit and KY78 primer, and Takara LA Taq DNA polymerase (Takara Shuzo Co., Ltd.), the first PCR was carried out. Using a part of the PCR product as a template, and the UTP primer attached to the kit and the KM2 primer, the second PCR was performed with Takara LA Taq DNA polymerase (Takara Shuzo Co., Ltd.) to obtain a PCR product. This PCR product was cloned into pGEM-T easy vector, and the nucleotide sequence was determined according to the above Step (D). The obtained HCV cDNA clone containing positions 1 to 709 in SEQ ID NO:1 was designated pTPF1-0007.

(F) Obtaining cDNA of 3'-Untranslated Region and Determining Its Nucleotide Sequence The RNA obtained in the above Step (A) was subjected to 3'-RACE to obtain cDNA at the end of the 3'-untranslated region. First, Poly(A) was added to the RNA of the patient using the Poly(A) Tailing Kit (Ambion) according to the instruction attached to the kit. The same operations as in the Steps (B) to (D) described above were carried out except that the dT-Adp primer was used instead of the XR58R primer; the 3UTR-1F primer and the Adp primer were used as the primers for the 1st PCR; and the XR58F and Adp primers were used as the primers for the 2nd PCR. The obtained HCV cDNA clone was designated pTPF1-8994.

The obtained HCV strain was designated the TPF1 stain. The TPF1 strain is an HCV having a total length of 9594 bases. Its nucleotide sequence is shown in SEQ ID NO:1 (wherein C at position 3277 is read as T; T at position 5752 is read as A; and A at position 6237 is read as G). The polynucleotide of the obtained TPF1 strain had a coding region encoding 3010 continuous amino acids between position 342 and position 9374. The amino acid sequence of the polyprotein of the TPF1 strain is shown in SEQ ID NO:2 (wherein the amino acid T (threonine) at amino acid position 979 is read as M (methionine); the amino acid L (leucine) at amino acid position 1804 is read as Q (glutamine); and the amino acid K (lysine) at amino acid position 1966 is read as E (glutamic acid).

The following are primers used for the cloning and the determination of nucleotide sequences.

```
XR58R (SEQ ID NO: 5):
5'-tcatgcggct cacggacctt tcacagctag-3'

HC-LongA1 (SEQ ID NO: 6):
5'-atcgtcttca cgcagaaagc gtctagccat-3'

1b9405R (SEQ ID NO: 7):
5'-gcctattggc ctggagtgtt tagctc-3'

HC85F (SEQ ID NO: 8):
5'-atggcgttag tatgagtgtc gtgcagcct-3'

HC9302R (SEQ ID NO: 9):
5'-tcgggcacga gacaggctgt gatatatgtc t-3'

Chiba-as (SEQ ID NO: 10):
5'-tgcacggtct acgagacct-3'

KY78 (SEQ ID NO: 11):
5'-ctcgcaagca ccctatcagc cagt-3'

KM2 (SEQ ID NO: 12):
5'-aggcattgag cgggtttat-3' dT-Adp (SEQ ID NO: 13):
5'-ctagactcga gtcgacatcg tttttttttt ttttttt-3'

3UTR-1F (SEQ ID NO: 14):
5'-atcttagccc tagtcacggc-3'

Adp (SEQ ID NO: 15):
5'-ctagactcga gtcgacatcg-3'

XR58F (SEQ ID NO: 16):
5'-ctagctgtaa aggtccgtga gccgcatga-3'

M13 Primer M3 (SEQ ID NO: 17):
5'-gtaaaacgac ggccagt-3'

M13 Primer RV (SEQ ID NO: 18):
5'-caggaaacag ctatgac-3'

104 (SEQ ID NO: 19):
5'-aggaagactt ccgagcggtc-3'

HC841S (SEQ ID NO: 20):
5'-ggaacttgcc cggttgctct ttctctatct tc-3'

E1 (SEQ ID NO: 21):
5'-attccatggt ggggaactgg gctaa-3'

HC2069S (SEQ ID NO: 22):
5'-taacaatacc ttgacctgcc ccacggactg-3'

HC2430S (SEQ ID NO: 23):
5'-aacatcgtgg acgtgcaata cctgtacgg-3'

HC2461AS (SEQ ID NO: 24):
5'-gaccctacac cgtacaggta-3'

HC2769S (SEQ ID NO: 25):
5'-ttggaccggg agatggctgc atcgtg-3'
```

-continued

HC3632F (SEQ ID NO: 26):
5'-cacccaaatg tacaccaatg t-3'

HC3928S (SEQ ID NO: 27):
5'-tacccgttga gtctatggaa ac-3'

HC4016AS (SEQ ID NO: 28):
5'-cacttggaat gtctgcggta-3'

HC4498S (SEQ ID NO: 29):
5'-aggggggggag gcatctcatt ttctg-3'

HC4888F (SEQ ID NO: 30):
5'-tgctatgacg cgggctgtgc ttggta-3'

HC5381F (SEQ ID NO: 31):
5'-ggtcattgtg ggcaggatca t-3'

HC5692S (SEQ ID NO: 32):
5'-ctgcctggaa accccgcgat-3'

HC5858F (SEQ ID NO: 33):
5'-tggcagcata ggccttggga aggt-3'

HC6315F (SEQ ID NO: 34):
5'-aagacctggc tccagtccaa g-3'

5A-1 (SEQ ID NO: 35):
5'-ttccatgctc accgacccct c-3'

HC7090S (SEQ ID NO: 36):
5'-gtggagtcag agaataaggt-3'

HC7743F (SEQ ID NO: 37):
5'-cagaagaagg tcacctttga c-3'

HC8192S (SEQ ID NO: 38):
5'-gcagcgggtc gagttcctgg tgaat-3'

HC8939F (SEQ ID NO: 39):
5'-ctacggggcc tgttactcca ttgaac-3'

(G) Preparation of Subgenomic RNA Replicon

The full-length polynucleotide of the hepatitis C virus TPF1 strain was inserted into the downstream of the T7 RNA promoter sequence in pBluescript II SK(+) (hereinafter referred to as pTPF1).

Thereafter, in pTPF1, a region from a part of the core region to the NS2 region, encoding structural protein and nonstructural protein, was replaced with a neomycin resistance gene (neomycin phosphotransferase, NPT-II) and EMCV-IRES (internal ribosomal entry site of encephalomyocarditis virus) to construct a plasmid DNA pRepTPF1. This plasmid was constructed by a procedure according to a previous report (Lohmann et al., Science, (1999) 285, pp. 110-113).

More specifically, pTPF1 was first digested with restriction enzymes AgeI and BsrGI. A fragment obtained by amplifying a sequence from the 5'-UTR to the core region derived from pTPF1 and a neomycin resistance gene derived from pcDNA3.1(+) by PCR and digesting the resulting amplification product with restriction enzymes AgeI and PmeI; and a fragment obtained by linking a sequence from EMCV-IRES to the NS3 region by PCR amplification and digesting the resulting product with restriction enzymes PmeI and BsrGI; were inserted into the above AgeI/BsrGI-digested pTPF1 by ligation, to obtain a plasmid DNA pRepTPF1.

Into this plasmid DNA pRepTPF1, mutations were introduced using the Quick Mutagenesis Kit (Stratagene) according to the method recommended by the manufacturer such that the nucleic acid corresponding to nucleotide position 5752 in SEQ ID NO:1 is substituted from A to T and the nucleic acid corresponding to nucleotide position 6237 is substituted from G to A. As a result, the amino acid corresponding to amino acid position 1804 in SEQ ID NO:2 was mutated from Q (glutamine) to L (leucine), and the amino acid corresponding to amino acid position 1966 was mutated from E (glutamic acid) to K (lysine). The plasmid DNA into which these amino acid substitutions were introduced was designated pRep4B.

The plasmid DNA pTPF1 containing the full-length HCV DNA prepared in (F) was digested with a restriction enzyme SfiI, and a fragment obtained by digesting pRep4B with a restriction enzyme SfiI was inserted into the above cleavage site by ligation, to prepare a plasmid DNA pTPF1/4B containing the full-length HCV DNA into which the appropriate mutations were inserted. The thus obtained HCV strain was designated the TPF 1/4B strain.

EXAMPLES

1. Introduction of Mutation into HCV NS2 Protease Region

Using the pTPF1/4B gene as a template, in the presence of the AgeI primer 5'-accggtgagtacaccggaattgccaggacg-3' (SEQ ID NO:40) and the FseI primer 5'-atttgggtgattgggcccttcgggc-cggcc-3' (SEQ ID NO:41), polymerase chain reaction (PCR) was performed using Takara LA Taq DNA polymerase (Takara Shuzo Co., Ltd.) by thermal cycling reaction by 20 cycles of 94° C. for 20 seconds and 68° C. for 4 minutes, to amplify the vicinity of the NS2 protease region in the TPF1/4B genome.

The amplified fragment was separated by 1.0% agarose gel electrophoresis, and the DNA fragment was recovered using the QIAquick gel purification kit (QIAGEN) according to the method recommended by the manufacturer. The recovered TPF1 fragment was ligated to pGEM-T easy vector (Promega) according to the method recommended by the manufacturer, and the DH5α strain was transformed with the obtained plasmid. A transformant which was resistant to ampicillin and formed a white colony in plate culture on agar medium supplemented with IPTG and X-gal was selected, and the selected transformant was cultured in 2YT medium supplemented with 100 μg/ml ampicillin. From the cultured bacterial cells, a plasmid pTPF1-AgeFse was purified using Wizard Plus SV Miniprep DNA Purification System.

The sequence of the TPF1 fragment incorporated in the purified plasmid was analyzed by performing reaction using the CEQ DTCS Quick Start Kit (Beckman Coulter) according to the method recommended by the manufacturer, with primers provided as appropriate that matches the vector and the HCV sequence, followed by analysis by the CEQ2000 XL DNA analysis system (Software version 4.0.0, Beckman Coulter). The obtained data was processed by Sequencher (Version 4.1.2, Gene Codes Corporation) for integration and analysis of the sequence data to confirm the nucleotide sequence of pTPF1-AgeFse.

Thereafter, the mutation at amino acid position 170 (from M to T) in NS2 protease was introduced into the pTPF1-AgeFse prepared as described above, using the Quick Mutagenesis kit (Stratagene) according to the method recommended by the manufacturer. The plasmid into which the amino acid substitution was introduced was designated pTPF1-AgeFseNpro.

Further, pTPF1/4B was digested with restriction enzymes AgeI and FseI, and the fragment derived from pTPF1-AgeFse/Npro prepared by digestion with AgeI and FseI was inserted into the above cleavage site by ligation. This plasmid was designated pTPF1-M.

2. Effect of Amino Acid Mutations on HCV RNA Replication

Using, as a template, each of pTPF1-M prepared in 1, which has the amino acid mutation, and pTPF1/4B, which does not have the sequence causing the mutation, RNA was synthesized with the Megascript T7 kit (Ambion) or AmpliScribe T7-Flash transcription kit (Epicentre). The RNA was purified according to the method recommended by the manufacturer.

Using Dulbecco's modified Eagle medium (D-MEM, IWAKI) supplemented with 10% fetal bovine serum (FBS), 50 U/mL penicillin and 50 μg/mL streptomycin as a medium, human liver cancer cells (Huh7, JCRB0403) were cultured under 5% carbon dioxide at 37° C. Cells before confluence were detached from the culture dish by treatment with trypsin and EDTA, and resuspended in a serum-containing medium to inactivate trypsin. The cells were washed twice with PBS, and resuspended in Cytomix (120 mM potassium chloride, 10 mM potassium phosphate, 5 mM magnesium chloride, 25 mM HEPES, 0.15 mM calcium chloride and 2 mM EGTA, pH7.6) supplemented with 1.25% DMSO. The resulting cell suspension was then transferred to an electroporation cuvette with a gap of 0.4 cm.

After adding 10 μg of RNA to the cells, the resulting mixture was sufficiently cooled on ice for 5 minutes. Using an electroporator (Bio-Rad), a pulse was applied to the cells at 960 μF at 250 V. The cells after transfection were immediately resuspended in 10 mL of a medium, and 1 mL each of the resulting suspension was placed in a 12-well plate (diameter, 22.1 mm), followed by starting culture. The culture supernatant was harvested at Hour 4, Hour 24, Hour 48 and Hour 72. After centrifuging the harvested culture supernatant at 2 k rpm for 10 minutes, the supernatant was recovered. Using a kit for the HCV core antigen (Fujirebio, Inc., LUMIPULSE), 100 μL of the supernatant was subjected to measurement.

Figure 2:
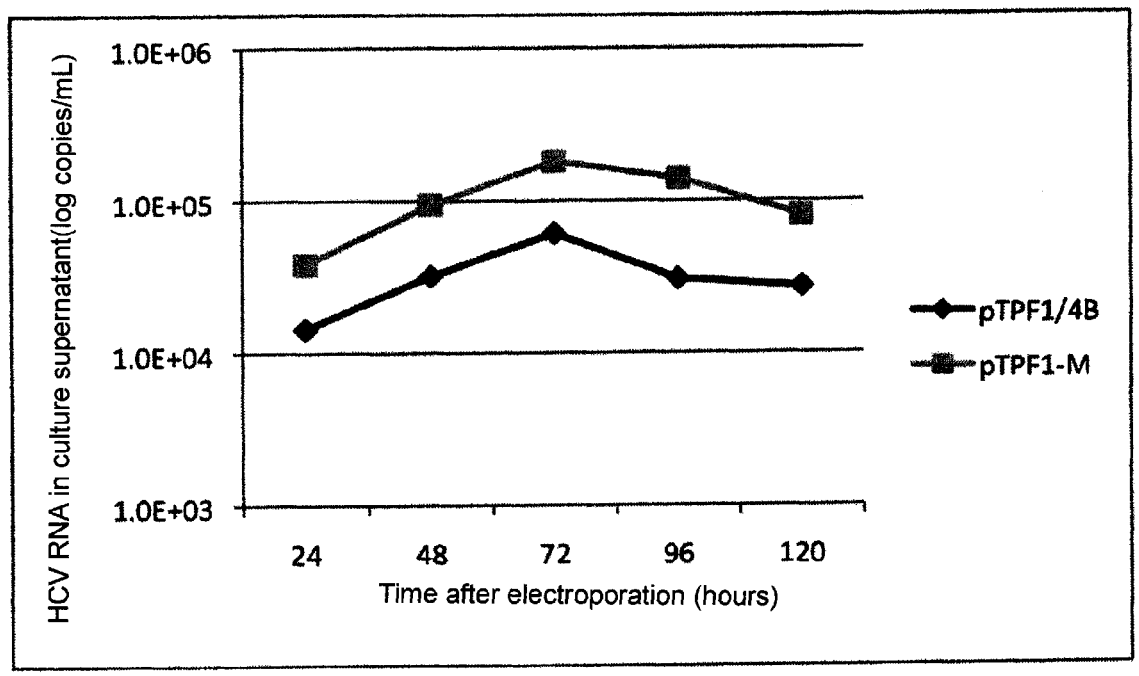
FIG. 2 is a diagram showing the relationship between the time after electroporation by which the RNA replicon having the HCV gene of the present invention (pTPF1-M) prepared in Example below was transfected into cells and the concentration of the HCV RNA secreted into the culture supernatant, together with the result for the HCV gene described in Patent Document 2 (pTPF1/4B).

As shown in FIG. 1, the measurement values of the core antigen in pTPF1-M and pTPF1/4B after transfection of the RNA into the cells using an electroporator were highest at Hour 72 after the electroporation, and the amount of the core antigen of pTPF1-M secreted was 2.8 times higher than that of pTPF1/4B. Further, the amount of HCV RNA secreted into the culture supernatant was highest at Hour 72 after the electroporation as in the case of the core antigen, and the amount of the HCV RNA in pTPF1-M was 3 times higher than that of pTPF1/4B (FIG. 2). This indicates that the pTPF1-M gene of the present invention having the mutation introduced in the NS2 protease region replicated in the cells and secreted the core antigen and the HCV RNA into the supernatant more efficiently than the pTPF1/4B gene. This means that the replication efficiency of the pTPF1-M gene is higher than that of pTPF1/4B.

3. Infection of Cultured Cells with HCV Particles

Whether or not the core antigen and the HCV RNA secreted into the culture supernatant in 2 form virus particles to allow reinfection in vitro was studied. More specifically, Huh7 cells were transfected with full-length HCV RNA synthesized from each of the pTPF1-M and pTPF1/4B genes, and the culture supernatant was harvested with time. The harvested culture supernatant was centrifuged at 15,000 rpm for 10 minutes and filtered (0.44 μm, Millipore) to remove cell debris and the like.

The supernatant after filtration was reacted for 6 hours at 37° C. with naive Huh7 cells cultured in a 12-well plate (diameter, 22.1 μm). Thereafter, the cells were washed 3 times with PBS. A fresh growth medium was added to the cells, and the cells were cultured in an incubator under 5% carbon dioxide at 37° C. For evaluation of the virus infectivity titer, the core antigen accumulated in the cells was visualized by immunostaining, and the number of cells positive for the core antigen was counted, to represent the number of infective virus particles contained in the culture supernatant with the focus-forming unit (FFU/mL).

More specifically, the cells 96 hours after the infection were fixed with methanol, and the fixed cells were incubated using 2% BSA-PBS for 2 hours at room temperature to perform blocking. Subsequently, an anti-core monoclonal antibody (1 μg/mL) as a primary antibody was added thereto, and the resulting mixture was incubated for 1 hour at room temperature. The cells were sufficiently washed, and an FITC-labeled secondary antibody was added thereto, followed by incubation of the resulting mixture for 1 hour at room temperature. HCV-infected cells were observed by counting the number of cells positive for the core antigen in the cells using an inverted fluorescence microscope.

Figure 3:
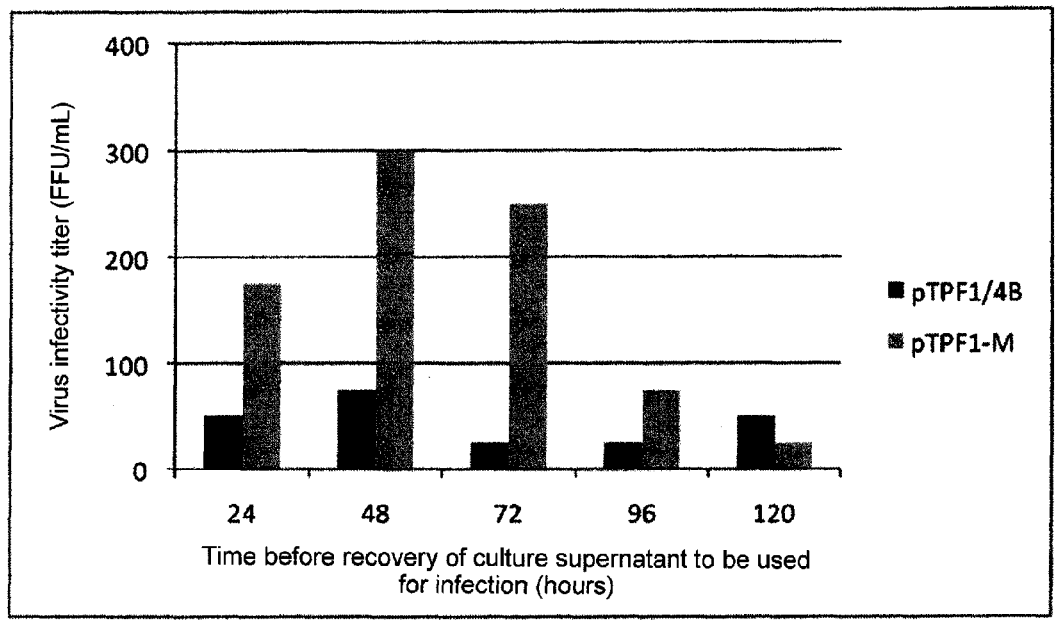
FIG. 3 is a diagram showing the relationship between the culture period after electroporation by which the RNA replicon having the HCV gene of the present invention (pTPF1-M) prepared in Example below was transfected into cells and the virus infectivity titer in the culture supernatant after the corresponding culture period, together with the result for the HCV gene described in Patent Document 2 (pTPF1/4B).

As shown in FIG. 3, in pTPF1-M having the mutation introduced in the NS2 protease region, the number of infectious virus particles released into the culture supernatant was largest (300 FFU/mL) at Hour 48 after the transfection of HCV RNA. On the other hand, in pTPF1/4B not having the amino acid mutation, although the number of infectious virus particles released into the culture supernatant was largest at Hour 48 (75 FFU/mL) after the transfection of HCV RNA, the value was as low as one-fourth of the value in pTPF1-M. Thus, it was shown that the cells into which the pTPF1-M gene was transfected released a larger number of infectious virus particles than the cells into which the pTPF1/4B gene was transfected. This indicates that the mutation in the NS2 protease region of the present invention improves the growth efficiency and the infection efficiency of the virus RNA.

4. Propagation of Virus in Monoclonal Huh7 Cells

Human liver cancer cells (Huh7, JCRB0403) were subjected to limiting dilution to obtain monoclonal cells, to newly establish the ALS32 cell. The propagation performance of pTPF1-M in ALS32 cells was evaluated by electroporation.

The human liver cancer cells (Huh7, JCRB0403) were cultured using, as a culture medium, D-MEM supplemented with 10% FBS, 50 U/mL penicillin and 50 μg/mL streptomycin, under 5% carbon dioxide at 37° C. The cells before confluence were detached from the culture dish by treatment with trypsin and EDTA, and resuspended in a serum-containing medium to inactivate trypsin. The number of cells was measured, and the cells were plated on a 96-well plate after adjusting its density using a growth medium such that 1 cell is contained per 1 well. After the plating, the culture was continued for 1 month, to establish the ALS32 cell.

Each of ALS32 cells and Huh7/JCRB0403 cells were cultured using, as a culture medium, D-MEM supplemented with 10% FBS, 50 U/mL penicillin and 50 μg/mL streptomycin, under 5% carbon dioxide at 37° C. The cells before confluence were detached from the culture dish by treatment with trypsin and EDTA, and resuspended in a serum-containing medium to inactivate trypsin. The cells were washed twice with PBS, and resuspended in Cytomix supplemented with 1.25% DMSO. The resulting cell suspension was then transferred to an electroporation cuvette with a gap of 0.4 cm.

To each of ALS32 cells and Huh7/JCRB0403 cells, 10 μg of the pTPF1-M RNA synthesized in Example 3 was added, and the resulting mixture was sufficiently cooled on ice for 5 minutes. Using an electroporator (Bio-Rad), a pulse was applied to the cells at 960 μF at 250 V. The cells after transfection were immediately resuspended in 10 mL of a medium, and 1 mL each of the resulting suspension was placed in a 12-well plate (diameter, 22.1 mm), followed by starting culture. The culture supernatant was harvested at Hour 24, Hour 48 Hour 72, Hour 96 and Hour 120. After centrifuging the harvested culture supernatant at 2 k rpm for 10 minutes, the supernatant was recovered. Using a kit for the HCV core antigen (Fujirebio, Inc., LUMIPULSE), 100 μL of the supernatant was subjected to measurement.

Figure 4:
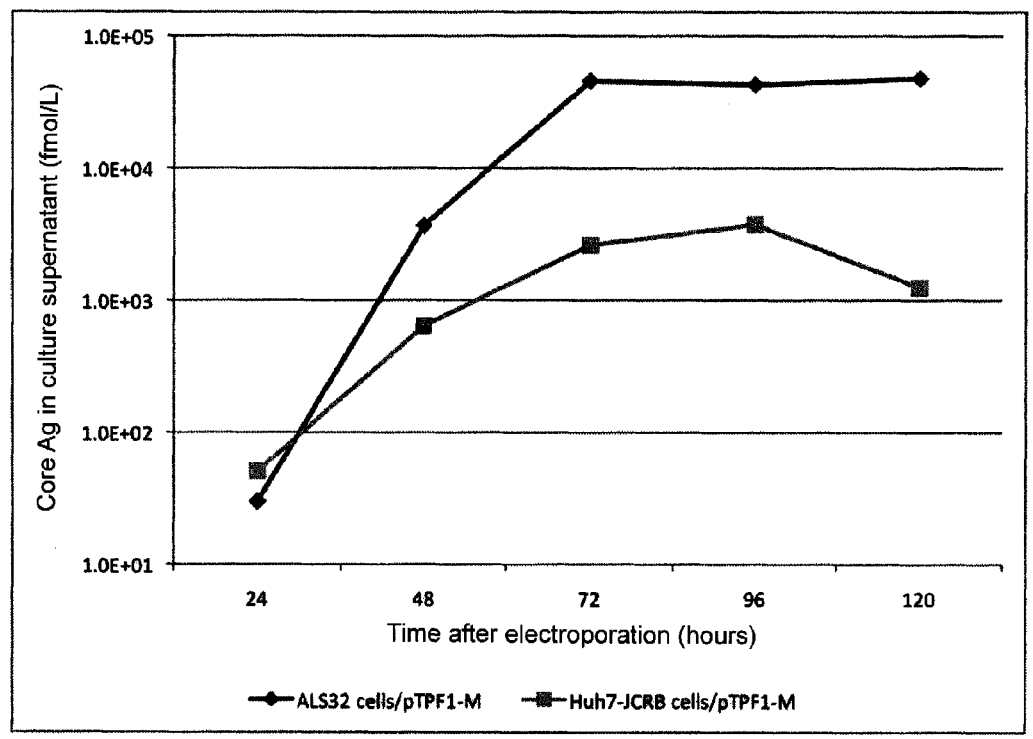
FIG. 4 is a diagram showing changes with time in the measured values of the core antigen in ALS32 cells and Huh7 cells after transfection of pTPF1-M RNA having the HCV gene of the present invention (pTPF1-M) prepared in Example below with an electroporator.
Figure 5:
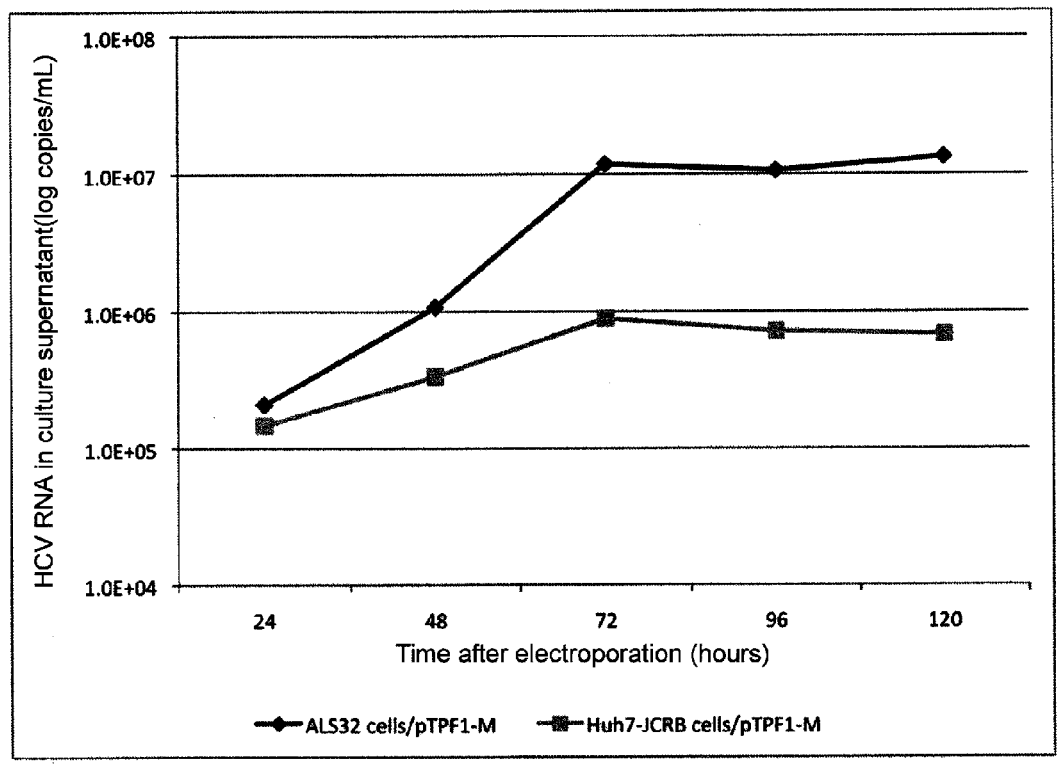
FIG. 5 is a diagram showing changes with time in the amounts of HCV RNA secreted into the culture supernatant of ALS32 cells and Huh7 cells after transfection of pTPF1-M RNA having the HCV gene of the present invention (pTPF1-M) prepared in Example below.

As shown in FIG. 4, the measurement values of the core antigen in the both types cells after transfection of pTPF1-M RNA using an electroporator were highest at Hour 72 to Hour 96 after the electroporation, and the amount of the core antigen of ALS32 cells secreted was 17.5 times larger than that of Huh7/JCRB0403 cells at Hour 72 after the electroporation. Further, the amounts of HCV RNA secreted into these culture supernatants were highest at Hour 72 after the electroporation, and the amount of HCV RNA from ALS32 cells was 13.4 times larger than that from Huh7/JCRB0403 cells (FIG. 5). This indicates that the pTPF1-M gene of the present invention having the mutation introduced in the NS2 protease region can more efficiently replicate in monoclonal ALS32 cells than in their parent cells.

5. Infection of Monoclonal Cultured Cells with HCV Particles

Whether or not the core antigen and the HCV RNA secreted into the culture supernatant in 4 form virus particles to allow reinfection in vitro was studied. More specifically, each of ALS32 cells and Huh7/JCRB0403 cells were transfected with full-length HCV RNA synthesized from the pTPF1-M gene, and the culture supernatant was harvested with time. The harvested culture supernatant was centrifuged at 15,000 rpm for 10 minutes and filtered (0.45 μm, Millipore) to remove cell debris and the like.

Each of the ALS32 cell-derived supernatant and the Huh7 cell-derived supernatant after filtration was reacted for 6 hours at 37° C. with naive ALS32 cultured cells or naive Huh7 cultured cells, respectively, cultured in a 12-well plate (diameter, 22.1 μm). Thereafter, the cells were washed 3 times with PBS. A fresh growth medium was added to the cells, and the cells were cultured in an incubator under 5% carbon dioxide at 37° C. For evaluation of the virus infectivity titer, the core antigen accumulated in the cells was visualized by immunostaining, and the number of cells positive for the core antigen was counted, to represent the number of infective virus particles contained in the culture supernatant with the focus-forming unit (FFU/mL).

More specifically, the cells 96 hours after the infection were fixed with methanol, and the fixed cells were incubated using 2% BSA-PBS for 2 hours at room temperature to perform blocking. Subsequently, an anti-core monoclonal antibody (1 μg/mL) as a primary antibody was added thereto, and the resulting mixture was incubated for 1 hour at room temperature. The cells were sufficiently washed, and an FITC-labeled secondary antibody was added thereto, followed by incubation of the resulting mixture for 1 hour at room temperature. HCV-infected cells were observed by counting the number of cells positive for the core antigen in the cells using an inverted fluorescence microscope.

Figure 6:
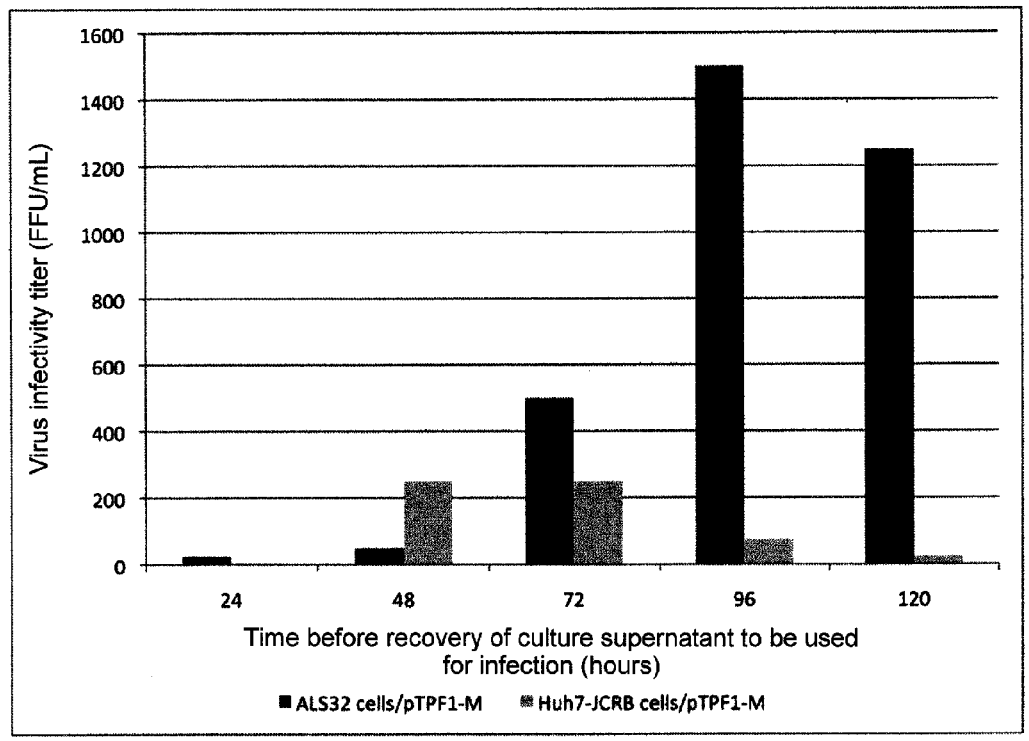
FIG. 6 is a diagram showing the result obtained by transfecting pTPF1-M RNA having the HCV gene of the present invention (pTPF1-M) prepared in Example below into each of ALS32 cells and Huh7 cells to allow secretion of virus particles formed from the HCV RNA into the culture supernatant, followed by infection of each of ALS32 cells and Huh7 cells with the virus particles. The relationship between the time period before harvest of the culture supernatant that was used for the infection and the virus infectivity titer is shown.

As shown in FIG. 6, it was confirmed that, when ALS32 cells were infected with virus particles obtained from the same type of cells, the number of infectious virus particles released into the culture supernatant was largest (1,500 FFU/mL) at Hour 96 after the transfection of HCV RNA. On the other hand, in the Huh7/JCRB0403 cells, although the number of infectious virus particles released into the culture supernatant was largest (250 FFU/mL) at Hour 48 to Hour 72 after the transfection of HCV RNA, the value was as low as one-sixth of the value in ALS32 cells. Thus, it was shown that the monoclonal ALS32 cells released a larger number of infectious virus particles than their parent cells, Huh7/JCRB0403. This indicates that the growth efficiency and the infection efficiency of the virus RNA having the mutation in the NS2 protease region can be improved by using ALS32 cells as monoclonal cells of Huh7/JCRB0403 cells.

Industrial Applicability

The RNA replicon of the present invention autonomously replicates by transfection into cells, and can more efficiently produce the hepatitis C virus gene, hepatitis C virus protein and infectious particles than pTPF1/4B RNA. As an in vitro model of hepatitis C virus infection, the replicon-replicating cell into which this replicon RNA was transfected reflects the mechanism of HCV propagation in vivo, and this replicon-replicating cell can therefore be used in a method for screening therapeutic drugs against HCV. Further, in addition to screening of therapeutic drugs against HCV, the screening method can be used for quality control in the production process of a therapeutic drug, so that the present method can also be used as a method for producing a pharmaceutical agent.

The invention claimed is:

1. A hepatitis C virus gene that encodes threonine as the 979th amino acid, leucine as the 1804th amino acid and lysine as the 1966th amino acid positions, wherein said amino acid positions correspond to the 979th, 1804th and 1966th positions, respectively, of the amino acid sequence shown in SEQ ID NO:2.

2. The gene according to claim 1, wherein the amino acid sequence encoded by said gene is the amino acid sequence shown in SEQ ID NO:2 or an amino acid sequence having a sequence identity of not less than 95% to said amino acid sequence shown in SEQ ID NO:2.

3. The gene according to claim 2, wherein said amino acid sequence encoded by said gene is the amino acid sequence shown in SEQ ID NO:2.

4. The gene according to claim 2, whose nucleotide sequence is the nucleotide sequence shown in SEQ ID NO:1 (wherein a DNA sequence uses "t" and an RNA sequence uses "u" at the same sequence positions) or a nucleotide sequence having a sequence identity of not less than 90% to said sequence.

5. The gene according to claim 4, whose nucleotide sequence is the nucleotide sequence shown in SEQ ID NO:1 (wherein a DNA sequence uses "t" and an RNA sequence uses "u" at the same sequence positions).

6. The gene according to any one of claims 1 to 5, whose genotype is the 1b type.

7. An RNA replicon comprising the gene according to claim 1.

8. A cell infected with the RNA replicon according to claim 7, said cell allows replication of hepatitis C virus.

9. A hepatitis C virus particle comprising the gene according to claim 1.

* * * * *

SEQUENCE LISTING

```
<160> NUMBER OF SEQ ID NOS: 41

<210> SEQ ID NO 1
<211> LENGTH: 9594
<212> TYPE: DNA
<213> ORGANISM: Hepatitis C virus
<220> FEATURE:
<221> NAME/KEY: CDS
<222> LOCATION: (342)..(9371)
<223> OTHER INFORMATION:

<400> SEQUENCE: 1
gccagccccc tgatgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
```

```
                                                                               -continued gtgcttgcga gtgccccggg aggtctcgta gaccgtgcat c atg agc aca aat cct              356
                                              Met Ser Thr Asn Pro
                                              1               5 aaa cct caa aga aaa acc aaa cgt aac acc aac cgc cgc cca cag gac                404
Lys Pro Gln Arg Lys Thr Lys Arg Asn Thr Asn Arg Arg Pro Gln Asp
            10              15              20 gtc aag ttc ccg ggt ggc cag atc gtt ggt gga gtt tac ctg ttg                    452
Val Lys Phe Pro Gly Gly Gln Ile Val Gly Gly Val Tyr Leu Leu
        25              30              35 ccg cgc agg ggc ccc agg ttg ggt gtg cgc gcg act agg aag act tcc                500
Pro Arg Arg Gly Pro Arg Leu Gly Val Arg Ala Thr Arg Lys Thr Ser
            40              45              50 gag cgg tcg caa cct cgt gga agg cga caa cct atc ccc aag gct cgc                548
Glu Arg Ser Gln Pro Arg Gly Arg Arg Gln Pro Ile Pro Lys Ala Arg
        55              60              65 cag ccc gag ggc agg gcc tgg gct cag ccc ggg tat cct tgg ccc ctc                596
Gln Pro Glu Gly Arg Ala Trp Ala Gln Pro Gly Tyr Pro Trp Pro Leu
70              75              80              85 tat ggc aac gag ggt ctg ggg tgg gca gga tgg ctc ctg tca ccc cgt                644
Tyr Gly Asn Glu Gly Leu Gly Trp Ala Gly Trp Leu Leu Ser Pro Arg
            90              95              100 ggc tct cgg cct agt tgg ggc ccc acg gac ccc cgg cgt agg tcg cgt                692
Gly Ser Arg Pro Ser Trp Gly Pro Thr Asp Pro Arg Arg Arg Ser Arg
        105             110             115 aat ttg ggt aag gtc atc gat acc ctc aca tgc ggc ttc gcc gac ctc                740
Asn Leu Gly Lys Val Ile Asp Thr Leu Thr Cys Gly Phe Ala Asp Leu
            120             125             130 atg ggg tac att ccg ctc gtc ggc gcc ccc cta gga ggc gct gcc agg                788
Met Gly Tyr Ile Pro Leu Val Gly Ala Pro Leu Gly Gly Ala Ala Arg
135             140             145 gcc ctg gcg cat ggc gtc cgg gtt ctg gag gac ggc gtg aac tat gca                836
Ala Leu Ala His Gly Val Arg Val Leu Glu Asp Gly Val Asn Tyr Ala
150             155             160             165 aca ggg aat ctg ccc ggt tgc cct ttc tct atc ttc ctc tta gct ttg                884
Thr Gly Asn Leu Pro Gly Cys Pro Phe Ser Ile Phe Leu Leu Ala Leu
            170             175             180 ctg tcc tgt ttg acc atc cca gct tcc gct cac gaa gtg cgc aac gta                932
Leu Ser Cys Leu Thr Ile Pro Ala Ser Ala His Glu Val Arg Asn Val
        185             190             195 tcc ggg ctg tac cat gtc acg aac gac tgc tcc aac tca agc att gtg                980
Ser Gly Leu Tyr His Val Thr Asn Asp Cys Ser Asn Ser Ser Ile Val
            200             205             210 tat gag gca gcg gac atg atc atg cac acc ccc ggg tgc gtg ccc tgc                1028
Tyr Glu Ala Ala Asp Met Ile Met His Thr Pro Gly Cys Val Pro Cys
215             220             225 gtc cgg gag ggt aac tcc tcc cgc tgc tgg gta gcg ctc act ccc acg                1076
Val Arg Glu Gly Asn Ser Ser Arg Cys Trp Val Ala Leu Thr Pro Thr
230             235             240             245 ctc gcg gcc agg aat agc agc gtc ccc act gcg aca ata cga cgc cat                1124
Leu Ala Ala Arg Asn Ser Ser Val Pro Thr Ala Thr Ile Arg Arg His
            250             255             260 gtc gat ttg ctc gtc ggg gcg gct gct ttc tgt tcc gct atg tac gtg                1172
Val Asp Leu Leu Val Gly Ala Ala Ala Phe Cys Ser Ala Met Tyr Val
        265             270             275 ggg gat ctt tgc gga tct gtt ttc ctc gtc tcc cag ctg ttc acc ttt                1220
Gly Asp Leu Cys Gly Ser Val Phe Leu Val Ser Gln Leu Phe Thr Phe
            280             285             290 tca cct cgc cgg tac gag acg gta cag gac tgc aat tgc tca ctc tat                1268
Ser Pro Arg Arg Tyr Glu Thr Val Gln Asp Cys Asn Cys Ser Leu Tyr
        295             300             305
```

```
ccc ggc cac gta tca ggc cat cgc atg gct tgg gat atg atg atg aac        1316
Pro Gly His Val Ser Gly His Arg Met Ala Trp Asp Met Met Met Asn
310             315                 320                 325 tgg tca cct aca aca gcc tta gtg gta tcg cag tta ctc cgg atc cca        1364
Trp Ser Pro Thr Thr Ala Leu Val Val Ser Gln Leu Leu Arg Ile Pro
            330                 335                 340 caa gcc gtc gtg gat atg gtg gta ggg gcc cac tgg gga gtc ctg gcg        1412
Gln Ala Val Val Asp Met Val Val Gly Ala His Trp Gly Val Leu Ala
                345                 350                 355 ggc ctt gcc tac tat tcc atg gtg ggg aac tgg gct aag gtc ttg att        1460
Gly Leu Ala Tyr Tyr Ser Met Val Gly Asn Trp Ala Lys Val Leu Ile
        360                 365                 370 gtg atg cta ctc ttt gcc ggc gtc gac ggg aag acc tac gtg aca ggg        1508
Val Met Leu Leu Phe Ala Gly Val Asp Gly Lys Thr Tyr Val Thr Gly
    375                 380                 385 ggg gcg cag agc cga gcc act caa ggc ttt gcg tcc ctc ttt aca cgg        1556
Gly Ala Gln Ser Arg Ala Thr Gln Gly Phe Ala Ser Leu Phe Thr Arg
390                 395                 400                 405 ggg ccg tct cag aaa ctc cag ctt gta aat tcc aac ggc agc tgg cac        1604
Gly Pro Ser Gln Lys Leu Gln Leu Val Asn Ser Asn Gly Ser Trp His
            410                 415                 420 att aac agg act gcc ttg aac tgc aat gac tcc ttc cag act ggg ttc        1652
Ile Asn Arg Thr Ala Leu Asn Cys Asn Asp Ser Phe Gln Thr Gly Phe
                425                 430                 435 ctt gcc gcg ctg ttt tac gca cac cgt ttc aac tcg tcc gga tgc cca        1700
Leu Ala Ala Leu Phe Tyr Ala His Arg Phe Asn Ser Ser Gly Cys Pro
                440                 445                 450 gag cgc atg gcc agc tgc cgc ccc atc gac acg ttc gat cag ggg tgg        1748
Glu Arg Met Ala Ser Cys Arg Pro Ile Asp Thr Phe Asp Gln Gly Trp
        455                 460                 465 ggc ccc atc act cat gtc gcg cgt cgc aca tcg gac cag agg cct tat        1796
Gly Pro Ile Thr His Val Ala Arg Arg Thr Ser Asp Gln Arg Pro Tyr
470                 475                 480                 485 tgc tgg cac tac gca cct caa ccg tgt ggt att gta ccc gcg ttg cag        1844
Cys Trp His Tyr Ala Pro Gln Pro Cys Gly Ile Val Pro Ala Leu Gln
            490                 495                 500 gta tgt ggt cca gtg tat tgc ttc acc cca agc ccc gtc gtg gtg ggg        1892
Val Cys Gly Pro Val Tyr Cys Phe Thr Pro Ser Pro Val Val Val Gly
                505                 510                 515 acg acc gat cgc ttc ggc gcc ccc acg tac aac tgg ggg gag aat gag        1940
Thr Thr Asp Arg Phe Gly Ala Pro Thr Tyr Asn Trp Gly Glu Asn Glu
                520                 525                 530 acg gac gtg cta ctc ctc aac aat acg cgg ccg ccg cac ggc aac tgg        1988
Thr Asp Val Leu Leu Leu Asn Asn Thr Arg Pro Pro His Gly Asn Trp
535                 540                 545 ttc ggc tgt aca tgg atg aat agt acc ggg ttc acc aag acg tgt ggg        2036
Phe Gly Cys Thr Trp Met Asn Ser Thr Gly Phe Thr Lys Thr Cys Gly
550                 555                 560                 565 ggc ccc ccc tgc aac atc ggg ggg ttt ggc aac aac acc ttg acc tgc        2084
Gly Pro Pro Cys Asn Ile Gly Gly Phe Gly Asn Asn Thr Leu Thr Cys
            570                 575                 580 cct acg gat tgc ttc cgg aag cac ccc gag gcc act tac acc aaa tgc        2132
Pro Thr Asp Cys Phe Arg Lys His Pro Glu Ala Thr Tyr Thr Lys Cys
                585                 590                 595 ggc tcg ggg ccc tgg ttg acg cct agg tgc atg gtt gat tac cca tac        2180
Gly Ser Gly Pro Trp Leu Thr Pro Arg Cys Met Val Asp Tyr Pro Tyr
            600                 605                 610 aga ctt tgg cac tac ccc tgc act gtt aac ttt tcc atc ttc aag gtc        2228
Arg Leu Trp His Tyr Pro Cys Thr Val Asn Phe Ser Ile Phe Lys Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 615 |     |     |     |     | 620 |     |     |     |     | 625 |     |     |     |      |
| agg | atg | tat | gtg | ggg | ggt | gtg | gag | cac | agg | ctc | acc | gcc | gcg | tgc | aat | 2276 |
| Arg | Met | Tyr | Val | Gly | Gly | Val | Glu | His | Arg | Leu | Thr | Ala | Ala | Cys | Asn |      |
| 630 |     |     |     |     | 635 |     |     |     |     | 640 |     |     |     |     | 645 |      |
| tgg | act | cgg | gga | gag | cgc | tgc | aac | ttg | gag | gat | agg | gac | aga | tcg | gag | 2324 |
| Trp | Thr | Arg | Gly | Glu | Arg | Cys | Asn | Leu | Glu | Asp | Arg | Asp | Arg | Ser | Glu |      |
|     |     |     |     | 650 |     |     |     |     | 655 |     |     |     |     | 660 |     |      |
| ctc | agc | ccg | ctg | cta | ctg | tct | acc | aca | gag | tgg | cag | gta | ctc | ccc | tgt | 2372 |
| Leu | Ser | Pro | Leu | Leu | Leu | Ser | Thr | Thr | Glu | Trp | Gln | Val | Leu | Pro | Cys |      |
|     |     |     | 665 |     |     |     |     | 670 |     |     |     |     | 675 |     |     |      |
| tct | ttc | acc | acc | tta | ccg | gcc | ctg | tcc | act | ggt | ttg | atc | cac | ctc | cac | 2420 |
| Ser | Phe | Thr | Thr | Leu | Pro | Ala | Leu | Ser | Thr | Gly | Leu | Ile | His | Leu | His |      |
|     | 680 |     |     |     |     | 685 |     |     |     |     | 690 |     |     |     |     |      |
| cag | aac | atc | gtg | gac | gtg | caa | tac | ctg | tac | ggt | gtg | ggg | tca | tcg | gtt | 2468 |
| Gln | Asn | Ile | Val | Asp | Val | Gln | Tyr | Leu | Tyr | Gly | Val | Gly | Ser | Ser | Val |      |
| 695 |     |     |     |     | 700 |     |     |     |     | 705 |     |     |     |     |     |      |
| gtc | tcc | att | gca | atc | agg | tgg | gag | tat | gtc | gtg | ctg | ctc | ttc | ctc | ctc | 2516 |
| Val | Ser | Ile | Ala | Ile | Arg | Trp | Glu | Tyr | Val | Val | Leu | Leu | Phe | Leu | Leu |      |
| 710 |     |     |     |     | 715 |     |     |     |     | 720 |     |     |     |     | 725 |      |
| ctg | gcg | gac | gcg | cgc | gtt | tgc | gcc | tgc | ttg | tgg | atg | atg | ctg | ctg | ata | 2564 |
| Leu | Ala | Asp | Ala | Arg | Val | Cys | Ala | Cys | Leu | Trp | Met | Met | Leu | Leu | Ile |      |
|     |     |     |     | 730 |     |     |     |     | 735 |     |     |     |     | 740 |     |      |
| gcc | caa | gct | gag | gcc | gcc | tta | gag | aac | ctg | gtg | atc | ctc | aat | gcg | gcg | 2612 |
| Ala | Gln | Ala | Glu | Ala | Ala | Leu | Glu | Asn | Leu | Val | Ile | Leu | Asn | Ala | Ala |      |
|     |     |     | 745 |     |     |     |     | 750 |     |     |     |     | 755 |     |     |      |
| tct | gtg | gcc | gga | gcg | cat | ggc | gtt | ctc | tct | ttc | ctt | gtg | ttc | ttc | tgc | 2660 |
| Ser | Val | Ala | Gly | Ala | His | Gly | Val | Leu | Ser | Phe | Leu | Val | Phe | Phe | Cys |      |
|     |     | 760 |     |     |     |     | 765 |     |     |     |     | 770 |     |     |     |      |
| gct | gcc | tgg | tac | atc | aag | ggc | aag | ctg | gtc | ccc | ggg | gcg | gca | tat | gcc | 2708 |
| Ala | Ala | Trp | Tyr | Ile | Lys | Gly | Lys | Leu | Val | Pro | Gly | Ala | Ala | Tyr | Ala |      |
|     | 775 |     |     |     |     | 780 |     |     |     |     | 785 |     |     |     |     |      |
| ttc | tat | ggt | gta | tgg | ccg | ctc | ctg | ctt | ctg | ctg | tca | tta | cca | cca | cga | 2756 |
| Phe | Tyr | Gly | Val | Trp | Pro | Leu | Leu | Leu | Leu | Leu | Ser | Leu | Pro | Pro |      |
| 790 |     |     |     |     | 795 |     |     |     |     | 800 |     |     |     |     | 805 |      |
| cga | gca | tac | gcc | ttg | gac | cgg | gag | atg | gct | gca | tcg | tgc | gga | ggc | gcg | 2804 |
| Arg | Ala | Tyr | Ala | Leu | Asp | Arg | Glu | Met | Ala | Ala | Ser | Cys | Gly | Gly | Ala |      |
|     |     |     | 810 |     |     |     |     | 815 |     |     |     |     | 820 |     |     |      |
| gtt | ttc | gta | ggt | ctg | atg | ctc | ctg | acc | ttg | tca | cca | cac | tac | aag | gtg | 2852 |
| Val | Phe | Val | Gly | Leu | Met | Leu | Leu | Thr | Leu | Ser | Pro | His | Tyr | Lys | Val |      |
|     |     | 825 |     |     |     |     | 830 |     |     |     |     | 835 |     |     |     |      |
| ttt | ctc | gct | agg | ctc | ata | tgg | tgg | tta | cag | tat | ttt | atc | acc | agg | gcc | 2900 |
| Phe | Leu | Ala | Arg | Leu | Ile | Trp | Trp | Leu | Gln | Tyr | Phe | Ile | Thr | Arg | Ala |      |
|     | 840 |     |     |     |     | 845 |     |     |     |     | 850 |     |     |     |     |      |
| gag | gcg | cac | ttg | cag | gtg | tgg | gtc | ccc | ccc | ctc | aac | gtt | cgg | ggg | ggc | 2948 |
| Glu | Ala | His | Leu | Gln | Val | Trp | Val | Pro | Pro | Leu | Asn | Val | Arg | Gly | Gly |      |
| 855 |     |     |     |     | 860 |     |     |     |     | 865 |     |     |     |     |     |      |
| cgc | gat | gcc | atc | atc | ctc | ctc | acg | tgt | gtg | gtc | cac | cca | gag | cta | att | 2996 |
| Arg | Asp | Ala | Ile | Ile | Leu | Leu | Thr | Cys | Val | Val | His | Pro | Glu | Leu | Ile |      |
| 870 |     |     |     |     | 875 |     |     |     |     | 880 |     |     |     |     | 885 |      |
| ttt | gac | atc | acc | aaa | atc | ttg | ctc | gcc | atg | ctc | ggt | ccg | ctc | atg | gtg | 3044 |
| Phe | Asp | Ile | Thr | Lys | Ile | Leu | Leu | Ala | Met | Leu | Gly | Pro | Leu | Met | Val |      |
|     |     |     |     | 890 |     |     |     |     | 895 |     |     |     |     | 900 |     |      |
| ctc | cag | gct | ggc | cta | act | aga | gtg | ccg | tac | ttc | gta | cgc | gct | caa | ggg | 3092 |
| Leu | Gln | Ala | Gly | Leu | Thr | Arg | Val | Pro | Tyr | Phe | Val | Arg | Ala | Gln | Gly |      |
|     |     |     | 905 |     |     |     |     | 910 |     |     |     |     | 915 |     |     |      |
| ctc | atc | cgt | gca | tgc | atg | tta | gtg | cgg | aaa | gtc | gct | ggg | ggc | cac | tat | 3140 |
| Leu | Ile | Arg | Ala | Cys | Met | Leu | Val | Arg | Lys | Val | Ala | Gly | Gly | His | Tyr |      |
|     |     | 920 |     |     |     |     | 925 |     |     |     |     | 930 |     |     |     |      |
| gtc | caa | atg | gcc | ctc | atg | aaa | ctg | gcc | gca | ctg | acg | ggt | acg | tac | gtt | 3188 |

|   |   |   |   |   |   |   |   |   |   |   |   |   |
|---|---|---|---|---|---|---|---|---|---|---|---|---|
| Val | Gln | Met | Ala | Leu | Met | Lys | Leu | Ala | Ala | Leu | Thr | Gly | Thr | Tyr | Val |
|  | 935 |  |  |  | 940 |  |  |  | 945 |  |  |  |  |  |  |

```
tat  gac  cat  ctt  act  ccg  ctg  cag  gac  tgg  gcc  cac  gcg  ggc  ttg  cga         3236
Tyr  Asp  His  Leu  Thr  Pro  Leu  Gln  Asp  Trp  Ala  His  Ala  Gly  Leu  Arg
950                 955                 960                 965 gac  ctt  gca  gtg  gca  gtt  gag  ccc  gtc  gtc  ttc  tct  gac  acg  gag  act         3284
Asp  Leu  Ala  Val  Ala  Val  Glu  Pro  Val  Val  Phe  Ser  Asp  Thr  Glu  Thr
                    970                 975                 980 aag  gtc  atc  acc  tgg  ggg  gca  gac  acc  gca  gcg  tgt  ggg  gac  atc  atc         3332
Lys  Val  Ile  Thr  Trp  Gly  Ala  Asp  Thr  Ala  Ala  Cys  Gly  Asp  Ile  Ile
               985                 990                 995 tcg  ggc  cta  ccc  gtc  tcc  gcc  cga  agg  ggg  agg  gag  ata  ctt  ctg              3377
Ser  Gly  Leu  Pro  Val  Ser  Ala  Arg  Arg  Gly  Arg  Glu  Ile  Leu  Leu
          1000                1005                1010 ggc  ccc  gcc  gac  agg  ttt  gga  gag  cag  ggg  tgg  cga  ctc  ctc  gcg              3422
Gly  Pro  Ala  Asp  Arg  Phe  Gly  Glu  Gln  Gly  Trp  Arg  Leu  Leu  Ala
          1015                1020                1025 cct  atc  acg  gct  tac  gct  caa  cag  acg  cgg  ggc  cta  ctt  ggc  tgt              3467
Pro  Ile  Thr  Ala  Tyr  Ala  Gln  Gln  Thr  Arg  Gly  Leu  Leu  Gly  Cys
          1030                1035                1040 atc  atc  acc  agc  ctc  aca  ggc  cgg  gac  aag  aac  cag  gtc  gag  ggg              3512
Ile  Ile  Thr  Ser  Leu  Thr  Gly  Arg  Asp  Lys  Asn  Gln  Val  Glu  Gly
          1045                1050                1055 gag  gtt  cag  gtg  gtt  tcc  acc  gca  acg  caa  tct  ttc  ctg  gcg  acc              3557
Glu  Val  Gln  Val  Val  Ser  Thr  Ala  Thr  Gln  Ser  Phe  Leu  Ala  Thr
          1060                1065                1070 tgc  gtc  aac  ggc  gtg  tgt  tgg  act  gtc  tac  cat  ggt  gcc  ggc  tcg              3602
Cys  Val  Asn  Gly  Val  Cys  Trp  Thr  Val  Tyr  His  Gly  Ala  Gly  Ser
          1075                1080                1085 aag  acc  ctg  gcc  ggc  ccg  aag  ggc  cca  atc  acc  caa  atg  tac  acc              3647
Lys  Thr  Leu  Ala  Gly  Pro  Lys  Gly  Pro  Ile  Thr  Gln  Met  Tyr  Thr
          1090                1095                1100 aat  gtg  gac  caa  gac  ctc  gtc  ggc  tgg  ccg  gcg  ccc  ccc  ggg  gcg              3692
Asn  Val  Asp  Gln  Asp  Leu  Val  Gly  Trp  Pro  Ala  Pro  Pro  Gly  Ala
          1105                1110                1115 cgc  tcc  ctg  aca  ccg  tgc  acc  tgc  ggc  agc  tcg  gac  ctc  tac  ctg              3737
Arg  Ser  Leu  Thr  Pro  Cys  Thr  Cys  Gly  Ser  Ser  Asp  Leu  Tyr  Leu
          1120                1125                1130 gtc  acg  agg  cat  gct  gat  gtc  att  ccg  gtg  cgc  cgg  cgg  ggc  gac              3782
Val  Thr  Arg  His  Ala  Asp  Val  Ile  Pro  Val  Arg  Arg  Arg  Gly  Asp
          1135                1140                1145 agc  agg  ggg  agt  cta  ctc  tct  ccc  agg  ccc  atc  tcc  tac  tta  aag              3827
Ser  Arg  Gly  Ser  Leu  Leu  Ser  Pro  Arg  Pro  Ile  Ser  Tyr  Leu  Lys
          1150                1155                1160 ggc  tcc  tca  ggt  ggt  cca  ctg  ctt  tgc  ccc  ctg  ggg  cac  gct  gtg              3872
Gly  Ser  Ser  Gly  Gly  Pro  Leu  Leu  Cys  Pro  Leu  Gly  His  Ala  Val
          1165                1170                1175 ggc  atc  ttc  cgg  gcc  gct  gtg  tgc  acc  cgg  ggg  gtt  gca  aag  gcg              3917
Gly  Ile  Phe  Arg  Ala  Ala  Val  Cys  Thr  Arg  Gly  Val  Ala  Lys  Ala
          1180                1185                1190 gtg  gat  ttt  gta  cct  gtt  gag  tct  atg  gaa  acc  acc  atg  cgg  tct              3962
Val  Asp  Phe  Val  Pro  Val  Glu  Ser  Met  Glu  Thr  Thr  Met  Arg  Ser
          1195                1200                1205 ccg  gtc  ttt  acg  gat  aat  tca  tct  ccc  ccg  gcc  gta  ccg  cag  aca              4007
Pro  Val  Phe  Thr  Asp  Asn  Ser  Ser  Pro  Pro  Ala  Val  Pro  Gln  Thr
          1210                1215                1220 ttc  caa  gtg  gcc  cat  cta  cac  gct  ccc  act  ggc  agt  ggc  aag  agc              4052
Phe  Gln  Val  Ala  His  Leu  His  Ala  Pro  Thr  Gly  Ser  Gly  Lys  Ser
          1225                1230                1235
```

|   |   |   |   |   |   |   |   |   |   |   |   |   |   |   |
|---|---|---|---|---|---|---|---|---|---|---|---|---|---|---|
| act | aag | gtg | ccg | gct | gcg | tac | gca | gcc | caa | ggg | tac | aag | gta | ctc | 4097 |
| Thr | Lys | Val | Pro | Ala | Ala | Tyr | Ala | Ala | Gln | Gly | Tyr | Lys | Val | Leu |
|     |     | 1240|     |     |     | 1245|     |     |     |     | 1250|     |     |     |

| gtc | ttg | aac | cca | tcc | gtt | gcc | gct | acc | tta | ggg | ttt | ggg | gcg | tac | 4142 |
|---|---|---|---|---|---|---|---|---|---|---|---|---|---|---|---|
| Val | Leu | Asn | Pro | Ser | Val | Ala | Ala | Thr | Leu | Gly | Phe | Gly | Ala | Tyr |
|     |     | 1255|     |     |     | 1260|     |     |     |     | 1265|     |     |     |

| atg | tct | aaa | gca | cat | ggt | gtt | gag | cct | aac | atc | aga | act | ggg | gta | 4187 |
|---|---|---|---|---|---|---|---|---|---|---|---|---|---|---|---|
| Met | Ser | Lys | Ala | His | Gly | Val | Glu | Pro | Asn | Ile | Arg | Thr | Gly | Val |
|     |     | 1270|     |     |     | 1275|     |     |     |     | 1280|     |     |     |

| agg | acc | atc | acc | acg | ggc | gct | tcc | atc | acg | tat | tcc | acc | tac | ggt | 4232 |
|---|---|---|---|---|---|---|---|---|---|---|---|---|---|---|---|
| Arg | Thr | Ile | Thr | Thr | Gly | Ala | Ser | Ile | Thr | Tyr | Ser | Thr | Tyr | Gly |
|     |     | 1285|     |     |     | 1290|     |     |     |     | 1295|     |     |     |

| aag | ttc | ctt | gcc | gac | ggt | ggt | tgc | tct | ggg | ggc | gcc | tat | gac | atc | 4277 |
|---|---|---|---|---|---|---|---|---|---|---|---|---|---|---|---|
| Lys | Phe | Leu | Ala | Asp | Gly | Gly | Cys | Ser | Gly | Gly | Ala | Tyr | Asp | Ile |
|     |     | 1300|     |     |     | 1305|     |     |     |     | 1310|     |     |     |

| ata | ata | tgt | gat | gag | tgc | cac | tca | act | gac | tcg | act | tcc | atc | ttg | 4322 |
|---|---|---|---|---|---|---|---|---|---|---|---|---|---|---|---|
| Ile | Ile | Cys | Asp | Glu | Cys | His | Ser | Thr | Asp | Ser | Thr | Ser | Ile | Leu |
|     |     | 1315|     |     |     | 1320|     |     |     |     | 1325|     |     |     |

| ggc | att | ggc | aca | gtc | ctg | gac | caa | gcg | gag | acg | gct | gga | gcg | cgg | 4367 |
|---|---|---|---|---|---|---|---|---|---|---|---|---|---|---|---|
| Gly | Ile | Gly | Thr | Val | Leu | Asp | Gln | Ala | Glu | Thr | Ala | Gly | Ala | Arg |
|     |     | 1330|     |     |     | 1335|     |     |     |     | 1340|     |     |     |

| ctc | gtc | gtg | ctc | gcc | acc | gct | acg | cct | ccg | gga | tcg | gtc | acc | gtg | 4412 |
|---|---|---|---|---|---|---|---|---|---|---|---|---|---|---|---|
| Leu | Val | Val | Leu | Ala | Thr | Ala | Thr | Pro | Pro | Gly | Ser | Val | Thr | Val |
|     |     | 1345|     |     |     | 1350|     |     |     |     | 1355|     |     |     |

| cca | cat | ccc | aat | atc | gag | gag | gtg | gcc | ttg | ccc | agc | acc | gga | gaa | 4457 |
|---|---|---|---|---|---|---|---|---|---|---|---|---|---|---|---|
| Pro | His | Pro | Asn | Ile | Glu | Glu | Val | Ala | Leu | Pro | Ser | Thr | Gly | Glu |
|     |     | 1360|     |     |     | 1365|     |     |     |     | 1370|     |     |     |

| att | ccc | ttc | tac | ggc | aaa | gcc | atc | ccc | att | gag | acc | atc | aag | ggg | 4502 |
|---|---|---|---|---|---|---|---|---|---|---|---|---|---|---|---|
| Ile | Pro | Phe | Tyr | Gly | Lys | Ala | Ile | Pro | Ile | Glu | Thr | Ile | Lys | Gly |
|     |     | 1375|     |     |     | 1380|     |     |     |     | 1385|     |     |     |

| ggg | agg | cac | ctc | atc | ttc | tgc | cac | tcc | aag | aag | aaa | tgt | gac | gag | 4547 |
|---|---|---|---|---|---|---|---|---|---|---|---|---|---|---|---|
| Gly | Arg | His | Leu | Ile | Phe | Cys | His | Ser | Lys | Lys | Lys | Cys | Asp | Glu |
|     |     | 1390|     |     |     | 1395|     |     |     |     | 1400|     |     |     |

| ctc | gct | gca | aag | ctg | gtg | ggc | ctc | gga | gtt | aac | gct | gtt | gcg | tac | 4592 |
|---|---|---|---|---|---|---|---|---|---|---|---|---|---|---|---|
| Leu | Ala | Ala | Lys | Leu | Val | Gly | Leu | Gly | Val | Asn | Ala | Val | Ala | Tyr |
|     |     | 1405|     |     |     | 1410|     |     |     |     | 1415|     |     |     |

| tac | cgg | ggt | ctt | gat | gtg | tcc | gtc | ata | cca | aca | agc | gga | gat | gtc | 4637 |
|---|---|---|---|---|---|---|---|---|---|---|---|---|---|---|---|
| Tyr | Arg | Gly | Leu | Asp | Val | Ser | Val | Ile | Pro | Thr | Ser | Gly | Asp | Val |
|     |     | 1420|     |     |     | 1425|     |     |     |     | 1430|     |     |     |

| gtt | gtc | gtg | gca | aca | gac | gct | cta | atg | acg | ggc | ttc | acc | ggc | gac | 4682 |
|---|---|---|---|---|---|---|---|---|---|---|---|---|---|---|---|
| Val | Val | Val | Ala | Thr | Asp | Ala | Leu | Met | Thr | Gly | Phe | Thr | Gly | Asp |
|     |     | 1435|     |     |     | 1440|     |     |     |     | 1445|     |     |     |

| ttt | gac | tca | gtg | atc | gac | tgt | aat | act | tgt | gtc | acc | cag | aca | gtt | 4727 |
|---|---|---|---|---|---|---|---|---|---|---|---|---|---|---|---|
| Phe | Asp | Ser | Val | Ile | Asp | Cys | Asn | Thr | Cys | Val | Thr | Gln | Thr | Val |
|     |     | 1450|     |     |     | 1455|     |     |     |     | 1460|     |     |     |

| gat | ttc | agc | ttg | gac | cct | acc | ttc | acc | att | gag | acg | aca | acc | gtg | 4772 |
|---|---|---|---|---|---|---|---|---|---|---|---|---|---|---|---|
| Asp | Phe | Ser | Leu | Asp | Pro | Thr | Phe | Thr | Ile | Glu | Thr | Thr | Thr | Val |
|     |     | 1465|     |     |     | 1470|     |     |     |     | 1475|     |     |     |

| ccc | caa | gac | gcg | gtg | tcg | cgt | tcg | cag | cga | cga | ggc | agg | act | ggc | 4817 |
|---|---|---|---|---|---|---|---|---|---|---|---|---|---|---|---|
| Pro | Gln | Asp | Ala | Val | Ser | Arg | Ser | Gln | Arg | Arg | Gly | Arg | Thr | Gly |
|     |     | 1480|     |     |     | 1485|     |     |     |     | 1490|     |     |     |

| agg | ggc | agg | atg | ggc | ata | tac | agg | ttt | gtg | gct | cca | ggg | gaa | cgg | 4862 |
|---|---|---|---|---|---|---|---|---|---|---|---|---|---|---|---|
| Arg | Gly | Arg | Met | Gly | Ile | Tyr | Arg | Phe | Val | Ala | Pro | Gly | Glu | Arg |
|     |     | 1495|     |     |     | 1500|     |     |     |     | 1505|     |     |     |

| ccc | tcg | ggc | atg | ttc | gat | tct | tcg | gtc | ctg | tgt | gag | tgc | tat | gac | 4907 |
|---|---|---|---|---|---|---|---|---|---|---|---|---|---|---|---|
| Pro | Ser | Gly | Met | Phe | Asp | Ser | Ser | Val | Leu | Cys | Glu | Cys | Tyr | Asp |
|     |     | 1510|     |     |     | 1515|     |     |     |     | 1520|     |     |     |

| gcg | ggc | tgt | gct | tgg | tat | gag | ctc | acg | ccc | gcc | gag | acc | tca | gtc | 4952 |
|---|---|---|---|---|---|---|---|---|---|---|---|---|---|---|---|
| Ala | Gly | Cys | Ala | Trp | Tyr | Glu | Leu | Thr | Pro | Ala | Glu | Thr | Ser | Val |
|     |     | 1525|     |     |     | 1530|     |     |     |     | 1535|     |     |     |

```
agg ttg cgg gct tac cta aat aca cca ggg ctg ccc gtc tgc cag      4997
Arg Leu Arg Ala Tyr Leu Asn Thr Pro Gly Leu Pro Val Cys Gln
        1540                1545                1550 gac cac ctg gag ttt tgg gag ggg gtc ttc aca ggc ctc acc cac      5042
Asp His Leu Glu Phe Trp Glu Gly Val Phe Thr Gly Leu Thr His
    1555                1560                1565 ata gat gcc cat ttc ttg tcc cag act aag cag gca gga gat aac      5087
Ile Asp Ala His Phe Leu Ser Gln Thr Lys Gln Ala Gly Asp Asn
1570                1575                1580 ttc ccc tac ctg gta gca tac cag gct acg gtg tgc gcc agg gcc      5132
Phe Pro Tyr Leu Val Ala Tyr Gln Ala Thr Val Cys Ala Arg Ala
            1585                1590                1595 cag gct ccc cct cca tcg tgg gat caa atg tgg aag tgt ctc ata      5177
Gln Ala Pro Pro Pro Ser Trp Asp Gln Met Trp Lys Cys Leu Ile
        1600                1605                1610 cgg ctg aag cct aca cta cac ggg cca acg ccc ctg ttg tat agg      5222
Arg Leu Lys Pro Thr Leu His Gly Pro Thr Pro Leu Leu Tyr Arg
    1615                1620                1625 cta gga gcc gtc cag aat gag gtc atc ctc aca cat ccc ata acc      5267
Leu Gly Ala Val Gln Asn Glu Val Ile Leu Thr His Pro Ile Thr
1630                1635                1640 aaa tac atc atg gca tgc atg tcg gct gac cta gag gtc gtc act      5312
Lys Tyr Ile Met Ala Cys Met Ser Ala Asp Leu Glu Val Val Thr
            1645                1650                1655 agc acc tgg gtg ctg gtc ggc ggg gtc ctt gca gct ctg gcc gcg      5357
Ser Thr Trp Val Leu Val Gly Gly Val Leu Ala Ala Leu Ala Ala
        1660                1665                1670 tac tgc ctg acg acg ggc agc gtg gtc att gtg ggc agg atc atc      5402
Tyr Cys Leu Thr Thr Gly Ser Val Val Ile Val Gly Arg Ile Ile
    1675                1680                1685 ttg tcc ggg aag ccg gct atc att cct gac agg gaa gtc ctc tac      5447
Leu Ser Gly Lys Pro Ala Ile Ile Pro Asp Arg Glu Val Leu Tyr
1690                1695                1700 cgg gag ttc gat gaa atg gaa gag tgt gcc tca cac ctc ccc tac      5492
Arg Glu Phe Asp Glu Met Glu Glu Cys Ala Ser His Leu Pro Tyr
            1705                1710                1715 atc gaa cag gga atg cag ctc gcc gaa caa ttc aag cag aag gcg      5537
Ile Glu Gln Gly Met Gln Leu Ala Glu Gln Phe Lys Gln Lys Ala
        1720                1725                1730 ctc ggg ttg ctg cag aca gcc acc aag caa gcg gaa gcc gct gct      5582
Leu Gly Leu Leu Gln Thr Ala Thr Lys Gln Ala Glu Ala Ala Ala
    1735                1740                1745 cct gtg gtg gag tcc aag tgg cga gcc ctt gag gcc ttc tgg gcg      5627
Pro Val Val Glu Ser Lys Trp Arg Ala Leu Glu Ala Phe Trp Ala
1750                1755                1760 aag cac atg tgg aat ttc atc agc ggg ata cag tac tta gca ggc      5672
Lys His Met Trp Asn Phe Ile Ser Gly Ile Gln Tyr Leu Ala Gly
            1765                1770                1775 ttg tcc act ctg cct ggg aac ccc gcg ata gca tca ctg atg gca      5717
Leu Ser Thr Leu Pro Gly Asn Pro Ala Ile Ala Ser Leu Met Ala
        1780                1785                1790 ttc aca gcc tct atc acc agc ccg ctt acc acc tta cac acc ctc      5762
Phe Thr Ala Ser Ile Thr Ser Pro Leu Thr Thr Leu His Thr Leu
    1795                1800                1805 ctg ttt aac atc ttg gga gga tgg gtg gcc gcc caa ctt gcc ccc      5807
Leu Phe Asn Ile Leu Gly Gly Trp Val Ala Ala Gln Leu Ala Pro
1810                1815                1820 ccc ggt gct gcc tcg gct ttc gtg ggc gcc ggc att gcc ggc gca      5852
Pro Gly Ala Ala Ser Ala Phe Val Gly Ala Gly Ile Ala Gly Ala
```

```
                1825                1830                1835
gct gtt ggc agc ata ggc ctt ggg aag gtg ctt gtg gac atc ctg      5897
Ala Val Gly Ser Ile Gly Leu Gly Lys Val Leu Val Asp Ile Leu
        1840                1845                1850 gcg ggt tat gga gca ggg gtg gca ggc gcg ctc gtg gcc ttc aag      5942
Ala Gly Tyr Gly Ala Gly Val Ala Gly Ala Leu Val Ala Phe Lys
        1855                1860                1865 gtc atg agc ggc gag atg ccc tcc acc gag gac ctg gtc aac tta      5987
Val Met Ser Gly Glu Met Pro Ser Thr Glu Asp Leu Val Asn Leu
        1870                1875                1880 ctc cct gcc atc ctc tct cct ggt gcc ctt gtc gtc ggg gtc gtg      6032
Leu Pro Ala Ile Leu Ser Pro Gly Ala Leu Val Val Gly Val Val
        1885                1890                1895 tgc gca gca ata ctg cgt cgg cat gtg ggc ccg ggg gag ggg gct      6077
Cys Ala Ala Ile Leu Arg Arg His Val Gly Pro Gly Glu Gly Ala
        1900                1905                1910 gtg caa tgg atg aac cgg ctg ata gcg ttc gcc tcg cgg ggt aac      6122
Val Gln Trp Met Asn Arg Leu Ile Ala Phe Ala Ser Arg Gly Asn
        1915                1920                1925 cac gtc tcc ccc acg cac tat gtg cct gag agc gac gct gca gcg      6167
His Val Ser Pro Thr His Tyr Val Pro Glu Ser Asp Ala Ala Ala
        1930                1935                1940 cgt gtc aca cag atc ctc tct agc ctc acc atc act cag cta ctg      6212
Arg Val Thr Gln Ile Leu Ser Ser Leu Thr Ile Thr Gln Leu Leu
        1945                1950                1955 aag agg ctc cac cag tgg att aat aag gac tgc tcc aca cca tgc      6257
Lys Arg Leu His Gln Trp Ile Asn Lys Asp Cys Ser Thr Pro Cys
        1960                1965                1970 tcc ggc tcg tgg ctt agg gac gtt tgg gac tgg ata tgc acg gtt      6302
Ser Gly Ser Trp Leu Arg Asp Val Trp Asp Trp Ile Cys Thr Val
        1975                1980                1985 ttg agt gac ttc aag acc tgg ctc cag tcc aag ctc ctg cca cgg      6347
Leu Ser Asp Phe Lys Thr Trp Leu Gln Ser Lys Leu Leu Pro Arg
        1990                1995                2000 tta ccg gga gtt cca ttc ctt tca tgc caa cgt ggg tat aag ggg      6392
Leu Pro Gly Val Pro Phe Leu Ser Cys Gln Arg Gly Tyr Lys Gly
        2005                2010                2015 gtc tgg cgg gga gat ggc atc atg cag acc tcc tgc cca tgt gga      6437
Val Trp Arg Gly Asp Gly Ile Met Gln Thr Ser Cys Pro Cys Gly
        2020                2025                2030 gca caa atc gcc gga cat gtc aag aac ggt tcc atg agg atc gtt      6482
Ala Gln Ile Ala Gly His Val Lys Asn Gly Ser Met Arg Ile Val
        2035                2040                2045 ggg cct aaa acc tgt agc aac acg tgg cac gga aca ttc ccc att      6527
Gly Pro Lys Thr Cys Ser Asn Thr Trp His Gly Thr Phe Pro Ile
        2050                2055                2060 aac gcg cac acc acg ggc ccc tgc aca ccc tcc cca gcg ccg aac      6572
Asn Ala His Thr Thr Gly Pro Cys Thr Pro Ser Pro Ala Pro Asn
        2065                2070                2075 tac tct aag gcg ttg tgg cgg gtg gct gct gag gag tac gtg gaa      6617
Tyr Ser Lys Ala Leu Trp Arg Val Ala Ala Glu Glu Tyr Val Glu
        2080                2085                2090 gtc acg cgg gtg ggg gat ttc cat tac gtg acg ggc atg acc act      6662
Val Thr Arg Val Gly Asp Phe His Tyr Val Thr Gly Met Thr Thr
        2095                2100                2105 gac aac gta aaa tgc cca tgc cag gtt ccg gcc ccc gaa ttc ttc      6707
Asp Asn Val Lys Cys Pro Cys Gln Val Pro Ala Pro Glu Phe Phe
        2110                2115                2120 aca gag gtg gat ggg gta cgg ctg cac agg tac gct ccg gcg tgc      6752
```

|   |   |   |   |   |   |   |   |   |   |   |   |   |
|---|---|---|---|---|---|---|---|---|---|---|---|---|
| Thr | Glu | Val<br>2125 | Asp | Gly | Val | Arg<br>2130 | Leu | His | Arg | Tyr<br>2135 | Ala | Pro | Ala | Cys |

| | | | | | | | | | | | | |
|---|---|---|---|---|---|---|---|---|---|---|---|---|
| aaa<br>Lys | cct<br>Pro | ctc<br>Leu<br>2140 | cta<br>Leu | cgg<br>Arg | gat<br>Asp | gag<br>Glu<br>2145 | gtc<br>Val | aca<br>Thr | ttc<br>Phe | cag<br>Gln<br>2150 | gtc<br>Val | ggg<br>Gly | ctc<br>Leu | aac<br>Asn | 6797 |

| cag<br>Gln | ttc<br>Phe | ccg<br>Pro<br>2155 | gtt<br>Val | ggg<br>Gly | tca<br>Ser | cag<br>Gln<br>2160 | ctc<br>Leu | cca<br>Pro | tgc<br>Cys | gag<br>Glu<br>2165 | ccc<br>Pro | gaa<br>Glu | ccg<br>Pro | gat<br>Asp | 6842 |

| gta<br>Val | tca<br>Ser | gtg<br>Val<br>2170 | ctc<br>Leu | act<br>Thr | tcc<br>Ser | atg<br>Met<br>2175 | ctt<br>Leu | acc<br>Thr | gac<br>Asp | cct<br>Pro<br>2180 | tcc<br>Ser | cac<br>His | atc<br>Ile | aca<br>Thr | 6887 |

| gca<br>Ala | gag<br>Glu | acg<br>Thr<br>2185 | gct<br>Ala | aag<br>Lys | cgt<br>Arg | agg<br>Arg<br>2190 | ctg<br>Leu | gcc<br>Ala | aga<br>Arg | ggg<br>Gly<br>2195 | tct<br>Ser | tcc<br>Ser | ccc<br>Pro | tct<br>Ser | 6932 |

| ttg<br>Leu | gcc<br>Ala | agc<br>Ser<br>2200 | tct<br>Ser | tca<br>Ser | gct<br>Ala | agt<br>Ser<br>2205 | cag<br>Gln | ttg<br>Leu | tct<br>Ser | gcg<br>Ala<br>2210 | ccc<br>Pro | tca<br>Ser | ttg<br>Leu | aag<br>Lys | 6977 |

| gcg<br>Ala | aca<br>Thr | tgc<br>Cys<br>2215 | acc<br>Thr | acc<br>Thr | cat<br>His | cat<br>His<br>2220 | gac<br>Asp | tcc<br>Ser | cca<br>Pro | gac<br>Asp<br>2225 | gct<br>Ala | gac<br>Asp | ctc<br>Leu | att<br>Ile | 7022 |

| gag<br>Glu | gcc<br>Ala | aac<br>Asn<br>2230 | ctc<br>Leu | ctg<br>Leu | tgg<br>Trp | cgg<br>Arg<br>2235 | cag<br>Gln | gag<br>Glu | atg<br>Met | gga<br>Gly<br>2240 | ggg<br>Gly | aac<br>Asn | atc<br>Ile | acc<br>Thr | 7067 |

| cgt<br>Arg | gtg<br>Val | gag<br>Glu<br>2245 | tca<br>Ser | gag<br>Glu | aac<br>Asn | aag<br>Lys<br>2250 | gtg<br>Val | gta<br>Val | atc<br>Ile | ctg<br>Leu<br>2255 | gac<br>Asp | tct<br>Ser | ttt<br>Phe | gac<br>Asp | 7112 |

| ccg<br>Pro | ctt<br>Leu | cga<br>Arg<br>2260 | gcg<br>Ala | gag<br>Glu | gag<br>Glu | gac<br>Asp<br>2265 | gag<br>Glu | agg<br>Arg | gag<br>Glu | gtg<br>Val<br>2270 | tct<br>Ser | gtt<br>Val | gcg<br>Ala | gcg<br>Ala | 7157 |

| gag<br>Glu | atc<br>Ile | ctg<br>Leu<br>2275 | cgg<br>Arg | aaa<br>Lys | acc<br>Thr | agg<br>Arg<br>2280 | aag<br>Lys | ttc<br>Phe | ccc<br>Pro | cca<br>Pro<br>2285 | gcg<br>Ala | atg<br>Met | ccc<br>Pro | ata<br>Ile | 7202 |

| tgg<br>Trp | gca<br>Ala | cgc<br>Arg<br>2290 | ccg<br>Pro | gac<br>Asp | tac<br>Tyr | aac<br>Asn<br>2295 | cca<br>Pro | ccg<br>Pro | ctg<br>Leu | cta<br>Leu<br>2300 | gag<br>Glu | act<br>Thr | tgg<br>Trp | aag<br>Lys | 7247 |

| gac<br>Asp | ccg<br>Pro | gac<br>Asp<br>2305 | tac<br>Tyr | gtc<br>Val | cct<br>Pro | cca<br>Pro<br>2310 | gtg<br>Val | gtg<br>Val | cac<br>His | ggg<br>Gly<br>2315 | tgc<br>Cys | cca<br>Pro | ttg<br>Leu | cca<br>Pro | 7292 |

| cct<br>Pro | acc<br>Thr | aag<br>Lys<br>2320 | acc<br>Thr | cct<br>Pro | cca<br>Pro | ata<br>Ile<br>2325 | cca<br>Pro | cct<br>Pro | ccg<br>Pro | cgg<br>Arg<br>2330 | agg<br>Arg | aaa<br>Lys | aag<br>Lys | aca<br>Thr | 7337 |

| gtt<br>Val | gtc<br>Val | ctg<br>Leu<br>2335 | aca<br>Thr | gag<br>Glu | tcc<br>Ser | acc<br>Thr<br>2340 | gtg<br>Val | tct<br>Ser | tct<br>Ser | gcc<br>Ala<br>2345 | ctg<br>Leu | gcg<br>Ala | gag<br>Glu | ctt<br>Leu | 7382 |

| gcc<br>Ala | aca<br>Thr | aag<br>Lys<br>2350 | acc<br>Thr | ttt<br>Phe | ggc<br>Gly | agc<br>Ser<br>2355 | tcc<br>Ser | gga<br>Gly | tcg<br>Ser | tcg<br>Ser<br>2360 | gcc<br>Ala | gtc<br>Val | gac<br>Asp | agc<br>Ser | 7427 |

| ggc<br>Gly | aca<br>Thr | gcg<br>Ala<br>2365 | acc<br>Thr | gcc<br>Ala | ccc<br>Pro | cct<br>Pro<br>2370 | aac<br>Asn | cag<br>Gln | ctc<br>Leu | tcc<br>Ser<br>2375 | gac<br>Asp | gaa<br>Glu | gtg<br>Val | gat<br>Asp | 7472 |

| aca<br>Thr | gga<br>Gly | tcc<br>Ser<br>2380 | gac<br>Asp | gtt<br>Val | gag<br>Glu | tcg<br>Ser<br>2385 | tac<br>Tyr | tcc<br>Ser | tcc<br>Ser | atg<br>Met<br>2390 | ccc<br>Pro | ccc<br>Pro | ctt<br>Leu | gag<br>Glu | 7517 |

| gga<br>Gly | gag<br>Glu | ccg<br>Pro<br>2395 | ggg<br>Gly | gac<br>Asp | ccc<br>Pro | gat<br>Asp<br>2400 | ctc<br>Leu | agc<br>Ser | gac<br>Asp | ggg<br>Gly<br>2405 | tct<br>Ser | tgg<br>Trp | tct<br>Ser | act<br>Thr | 7562 |

| gta<br>Val | agt<br>Ser | gag<br>Glu<br>2410 | gag<br>Glu | gct<br>Ala | ggt<br>Gly | gag<br>Glu<br>2415 | gac<br>Asp | gtc<br>Val | gtc<br>Val | tgc<br>Cys<br>2420 | tgc<br>Cys | tcg<br>Ser | atg<br>Met | tcc<br>Ser | 7607 |

-continued

| | | |
|---|---|---|
| tac aca tgg aca ggc gcc ttg atc acg ccg tgc gcc gcg gag gag<br>Tyr Thr Trp Thr Gly Ala Leu Ile Thr Pro Cys Ala Ala Glu Glu<br>2425                        2430                       2435 | 7652 |
| agc aag ctg ccc atc aat gcg ctg agc aac tct ttg ctg cgc cac<br>Ser Lys Leu Pro Ile Asn Ala Leu Ser Asn Ser Leu Leu Arg His<br>2440                        2445                       2450 | 7697 |
| cac aac atg gtc tat gcc aca aca tcc cgc agc gca agc caa cgg<br>His Asn Met Val Tyr Ala Thr Thr Ser Arg Ser Ala Ser Gln Arg<br>2455                        2460                       2465 | 7742 |
| cag aaa aag gtc acc ttt gac aga ctg caa gtc ctg gac gac cat<br>Gln Lys Lys Val Thr Phe Asp Arg Leu Gln Val Leu Asp Asp His<br>2470                        2475                       2480 | 7787 |
| tac cgg gac gtg ctc aag gag atg aag gcg aag gcg tcc aca gtt<br>Tyr Arg Asp Val Leu Lys Glu Met Lys Ala Lys Ala Ser Thr Val<br>2485                        2490                       2495 | 7832 |
| aag gct aaa ctt cta tcc gta gaa gag gcc tgc aag ctg acg ccc<br>Lys Ala Lys Leu Leu Ser Val Glu Glu Ala Cys Lys Leu Thr Pro<br>2500                        2505                       2510 | 7877 |
| cca cac tca gcc agg tcc aaa ttt ggc tat ggg gcg aag gac gtc<br>Pro His Ser Ala Arg Ser Lys Phe Gly Tyr Gly Ala Lys Asp Val<br>2515                        2520                       2525 | 7922 |
| cgg aac cta tcc agc aag gcc gtt aac cac atc aac tcc gtg tgg<br>Arg Asn Leu Ser Ser Lys Ala Val Asn His Ile Asn Ser Val Trp<br>2530                        2535                       2540 | 7967 |
| aag gac ttg ctg gaa gac act gag aca cca att gac acc acc atc<br>Lys Asp Leu Leu Glu Asp Thr Glu Thr Pro Ile Asp Thr Thr Ile<br>2545                        2550                       2555 | 8012 |
| atg gca aaa aat gag gtc ttc tgt gtt caa cca gag aag gga ggc<br>Met Ala Lys Asn Glu Val Phe Cys Val Gln Pro Glu Lys Gly Gly<br>2560                        2565                       2570 | 8057 |
| cgc aag cca gct cgc ctt atc gta tac cca gac ttg ggg gtg cgt<br>Arg Lys Pro Ala Arg Leu Ile Val Tyr Pro Asp Leu Gly Val Arg<br>2575                        2580                       2585 | 8102 |
| gtg tgc gag aaa atg gcc ctt tac gac gtg gtc tcc act ctt cct<br>Val Cys Glu Lys Met Ala Leu Tyr Asp Val Val Ser Thr Leu Pro<br>2590                        2595                       2600 | 8147 |
| cag gcc gtg atg ggc tcc tca tac gga ttc cag tac tct cct ggg<br>Gln Ala Val Met Gly Ser Ser Tyr Gly Phe Gln Tyr Ser Pro Gly<br>2605                        2610                       2615 | 8192 |
| cag cgg gtc gag ttc ctg gtg aat gcc tgg aaa tca aag aag aac<br>Gln Arg Val Glu Phe Leu Val Asn Ala Trp Lys Ser Lys Lys Asn<br>2620                        2625                       2630 | 8237 |
| cct atg ggc ttc gca tat gac acc cgc tgt ttt gac tca acg gtc<br>Pro Met Gly Phe Ala Tyr Asp Thr Arg Cys Phe Asp Ser Thr Val<br>2635                        2640                       2645 | 8282 |
| acc gag aac gac atc cgt gtt gag gag tca att tac caa tgt tgt<br>Thr Glu Asn Asp Ile Arg Val Glu Glu Ser Ile Tyr Gln Cys Cys<br>2650                        2655                       2660 | 8327 |
| gac ttg gcc ccc gag gcc aga cag gtg ata agg tcg ctc aca gag<br>Asp Leu Ala Pro Glu Ala Arg Gln Val Ile Arg Ser Leu Thr Glu<br>2665                        2670                       2675 | 8372 |
| cgg ctt tat gtc ggg ggc ccc ctg act aat tca aaa ggg cag aac<br>Arg Leu Tyr Val Gly Gly Pro Leu Thr Asn Ser Lys Gly Gln Asn<br>2680                        2685                       2690 | 8417 |
| tgc ggt tat cgc cgg tgc cgc gcc agc ggc gtg ctg acg act agc<br>Cys Gly Tyr Arg Arg Cys Arg Ala Ser Gly Val Leu Thr Thr Ser<br>2695                        2700                       2705 | 8462 |
| tgc ggt aat acc ctc aca tgt tac ttg aag gcc tct gca gcc tgt<br>Cys Gly Asn Thr Leu Thr Cys Tyr Leu Lys Ala Ser Ala Ala Cys<br>2710                        2715                       2720 | 8507 |

| | | | | | | | | | | | |
|---|---|---|---|---|---|---|---|---|---|---|---|
| cga | gct | gca | aag | ctc | cag | gac | tgc | acg | atg | ctc | gtg | tgc | ggg | gac | 8552 |
| Arg | Ala | Ala | Lys | Leu | Gln | Asp | Cys | Thr | Met | Leu | Val | Cys | Gly | Asp |  |
|  |  | 2725 |  |  |  | 2730 |  |  |  | 2735 |  |  |  |  |  |

| gac | ctt | gtc | gtt | atc | tgt | gaa | agc | gcg | ggg | acc | cag | gag | gac | gcg | 8597 |
| Asp | Leu | Val | Val | Ile | Cys | Glu | Ser | Ala | Gly | Thr | Gln | Glu | Asp | Ala |  |
|  |  | 2740 |  |  |  | 2745 |  |  |  | 2750 |  |  |  |  |  |

| gcg | agc | cta | cga | gtc | ttc | acg | gag | gct | atg | act | agg | tac | tcc | gcc | 8642 |
| Ala | Ser | Leu | Arg | Val | Phe | Thr | Glu | Ala | Met | Thr | Arg | Tyr | Ser | Ala |  |
|  |  | 2755 |  |  |  | 2760 |  |  |  | 2765 |  |  |  |  |  |

| ccc | ccc | ggg | gac | ccg | ccc | cga | ccg | gaa | tac | gac | ttg | gag | ttg | ata | 8687 |
| Pro | Pro | Gly | Asp | Pro | Pro | Arg | Pro | Glu | Tyr | Asp | Leu | Glu | Leu | Ile |  |
|  |  | 2770 |  |  |  | 2775 |  |  |  | 2780 |  |  |  |  |  |

| aca | tca | tgc | tcc | tcc | aac | gtg | tcg | gtc | gcg | cac | gat | gca | tct | ggc | 8732 |
| Thr | Ser | Cys | Ser | Ser | Asn | Val | Ser | Val | Ala | His | Asp | Ala | Ser | Gly |  |
|  |  | 2785 |  |  |  | 2790 |  |  |  | 2795 |  |  |  |  |  |

| aaa | cgg | gtg | tat | tac | ctc | acc | cgt | gac | ccc | acc | acc | ccc | ctt | gcg | 8777 |
| Lys | Arg | Val | Tyr | Tyr | Leu | Thr | Arg | Asp | Pro | Thr | Thr | Pro | Leu | Ala |  |
|  |  | 2800 |  |  |  | 2805 |  |  |  | 2810 |  |  |  |  |  |

| cgg | gct | gcg | tgg | gag | aca | gct | aaa | cac | act | cca | gtc | aac | tcc | tgg | 8822 |
| Arg | Ala | Ala | Trp | Glu | Thr | Ala | Lys | His | Thr | Pro | Val | Asn | Ser | Trp |  |
|  |  | 2815 |  |  |  | 2820 |  |  |  | 2825 |  |  |  |  |  |

| cta | ggc | aac | atc | atc | atg | tat | gcg | ccc | acc | ctc | tgg | gca | agg | atg | 8867 |
| Leu | Gly | Asn | Ile | Ile | Met | Tyr | Ala | Pro | Thr | Leu | Trp | Ala | Arg | Met |  |
|  |  | 2830 |  |  |  | 2835 |  |  |  | 2840 |  |  |  |  |  |

| att | ctg | atg | act | cac | ttc | ttc | tcc | atc | ctt | cta | gct | cag | gag | cag | 8912 |
| Ile | Leu | Met | Thr | His | Phe | Phe | Ser | Ile | Leu | Leu | Ala | Gln | Glu | Gln |  |
|  |  | 2845 |  |  |  | 2850 |  |  |  | 2855 |  |  |  |  |  |

| ctt | gaa | aaa | gcc | ctg | gat | tgt | cag | atc | tac | ggg | gcc | act | tac | tcc | 8957 |
| Leu | Glu | Lys | Ala | Leu | Asp | Cys | Gln | Ile | Tyr | Gly | Ala | Thr | Tyr | Ser |  |
|  |  | 2860 |  |  |  | 2865 |  |  |  | 2870 |  |  |  |  |  |

| att | gaa | cca | ctt | gac | cta | cct | cag | atc | att | caa | cga | ctc | cat | ggt | 9002 |
| Ile | Glu | Pro | Leu | Asp | Leu | Pro | Gln | Ile | Ile | Gln | Arg | Leu | His | Gly |  |
|  |  | 2875 |  |  |  | 2880 |  |  |  | 2885 |  |  |  |  |  |

| ctt | agc | gca | ttc | tca | ctc | cat | agt | tac | tct | cca | ggt | gaa | atc | aat | 9047 |
| Leu | Ser | Ala | Phe | Ser | Leu | His | Ser | Tyr | Ser | Pro | Gly | Glu | Ile | Asn |  |
|  |  | 2890 |  |  |  | 2895 |  |  |  | 2900 |  |  |  |  |  |

| agg | gtg | gct | tca | tgc | ctc | agg | aaa | ctt | ggg | gta | ccg | ccc | ttg | cga | 9092 |
| Arg | Val | Ala | Ser | Cys | Leu | Arg | Lys | Leu | Gly | Val | Pro | Pro | Leu | Arg |  |
|  |  | 2905 |  |  |  | 2910 |  |  |  | 2915 |  |  |  |  |  |

| gtc | tgg | aga | cat | cgg | gcc | aga | agt | gtc | cgc | gct | aag | cta | ctg | tcc | 9137 |
| Val | Trp | Arg | His | Arg | Ala | Arg | Ser | Val | Arg | Ala | Lys | Leu | Leu | Ser |  |
|  |  | 2920 |  |  |  | 2925 |  |  |  | 2930 |  |  |  |  |  |

| cag | ggg | ggg | agg | gct | gcc | act | tgt | ggc | aag | tac | ctc | ttc | aac | tgg | 9182 |
| Gln | Gly | Gly | Arg | Ala | Ala | Thr | Cys | Gly | Lys | Tyr | Leu | Phe | Asn | Trp |  |
|  |  | 2935 |  |  |  | 2940 |  |  |  | 2945 |  |  |  |  |  |

| gca | gta | agg | acc | aag | ctc | aaa | ctc | act | cca | atc | ccg | gct | gcg | tcc | 9227 |
| Ala | Val | Arg | Thr | Lys | Leu | Lys | Leu | Thr | Pro | Ile | Pro | Ala | Ala | Ser |  |
|  |  | 2950 |  |  |  | 2955 |  |  |  | 2960 |  |  |  |  |  |

| cag | ttg | gac | ttg | tcc | ggc | tgg | ttc | att | gct | ggt | tac | agc | ggg | gga | 9272 |
| Gln | Leu | Asp | Leu | Ser | Gly | Trp | Phe | Ile | Ala | Gly | Tyr | Ser | Gly | Gly |  |
|  |  | 2965 |  |  |  | 2970 |  |  |  | 2975 |  |  |  |  |  |

| gac | ata | tat | cac | agc | ctg | tct | cgt | gcc | cga | ccc | cgc | tgg | ttt | atg | 9317 |
| Asp | Ile | Tyr | His | Ser | Leu | Ser | Arg | Ala | Arg | Pro | Arg | Trp | Phe | Met |  |
|  |  | 2980 |  |  |  | 2985 |  |  |  | 2990 |  |  |  |  |  |

| ttg | tgc | cta | ctc | cta | ctt | tct | gtg | ggg | gta | ggc | atc | tac | ctg | ctc | 9362 |
| Leu | Cys | Leu | Leu | Leu | Leu | Ser | Val | Gly | Val | Gly | Ile | Tyr | Leu | Leu |  |
|  |  | 2995 |  |  |  | 3000 |  |  |  | 3005 |  |  |  |  |  |

| ccc | aat | cga | tgaacgggg | gctaaacact | ccaggccaat | aggccattct |  | 9411 |
| Pro | Asn | Arg |  |  |  |  |  |  |

```
                3010
gtttttttttt tttttttttt tttttttttt tttttttttt tttttttttt tttttccttt    9471
tttttttttt ttttcccttt cttttggtgg ctccatcttta gccctagtca cggctagctg    9531
tgaaaggtcc gtgagccgca tgactgcaga gagtgctgat actggcctct ctgcagatca    9591
tgt                                                                    9594
```

<210> SEQ ID NO 2
<211> LENGTH: 3010
<212> TYPE: PRT
<213> ORGANISM: Hepatitis C virus

<400> SEQUENCE: 2

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Pro Phe Ser Ile
                165                 170                 175

Phe Leu Leu Ala Leu Leu Ser Cys Leu Thr Ile Pro Ala Ser Ala His
            180                 185                 190

Glu Val Arg Asn Val Ser Gly Leu Tyr His Val Thr Asn Asp Cys Ser
        195                 200                 205

Asn Ser Ser Ile Val Tyr Glu Ala Ala Asp Met Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Val Pro Thr Ala
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
```

```
                        325                 330                 335
Leu Leu Arg Ile Pro Gln Ala Val Val Asp Met Val Val Gly Ala His
                340                 345                 350
Trp Gly Val Leu Ala Gly Leu Ala Tyr Tyr Ser Met Val Gly Asn Trp
                355                 360                 365
Ala Lys Val Leu Ile Val Met Leu Leu Phe Ala Gly Val Asp Gly Lys
            370                 375                 380
Thr Tyr Val Thr Gly Gly Ala Gln Ser Arg Ala Thr Gln Gly Phe Ala
385                 390                 395                 400
Ser Leu Phe Thr Arg Gly Pro Ser Gln Lys Leu Gln Leu Val Asn Ser
                405                 410                 415
Asn Gly Ser Trp His Ile Asn Arg Thr Ala Leu Asn Cys Asn Asp Ser
                420                 425                 430
Phe Gln Thr Gly Phe Leu Ala Ala Leu Phe Tyr Ala His Arg Phe Asn
                435                 440                 445
Ser Ser Gly Cys Pro Glu Arg Met Ala Ser Cys Arg Pro Ile Asp Thr
            450                 455                 460
Phe Asp Gln Gly Trp Gly Pro Ile Thr His Val Ala Arg Arg Thr Ser
465                 470                 475                 480
Asp Gln Arg Pro Tyr Cys Trp His Tyr Ala Pro Gln Pro Cys Gly Ile
                485                 490                 495
Val Pro Ala Leu Gln Val Cys Gly Pro Val Tyr Cys Phe Thr Pro Ser
            500                 505                 510
Pro Val Val Val Gly Thr Thr Asp Arg Phe Gly Ala Pro Thr Tyr Asn
            515                 520                 525
Trp Gly Glu Asn Glu Thr Asp Val Leu Leu Leu Asn Asn Thr Arg Pro
            530                 535                 540
Pro His Gly Asn Trp Phe Gly Cys Thr Trp Met Asn Ser Thr Gly Phe
545                 550                 555                 560
Thr Lys Thr Cys Gly Gly Pro Pro Cys Asn Ile Gly Gly Phe Gly Asn
                565                 570                 575
Asn Thr Leu Thr Cys Pro Thr Asp Cys Phe Arg Lys His Pro Glu Ala
            580                 585                 590
Thr Tyr Thr Lys Cys Gly Ser Gly Pro Trp Leu Thr Pro Arg Cys Met
            595                 600                 605
Val Asp Tyr Pro Tyr Arg Leu Trp His Tyr Pro Cys Thr Val Asn Phe
            610                 615                 620
Ser Ile Phe Lys Val Arg Met Tyr Val Gly Gly Val Glu His Arg Leu
625                 630                 635                 640
Thr Ala Ala Cys Asn Trp Thr Arg Gly Glu Arg Cys Asn Leu Glu Asp
                645                 650                 655
Arg Asp Arg Ser Glu Leu Ser Pro Leu Leu Leu Ser Thr Thr Glu Trp
                660                 665                 670
Gln Val Leu Pro Cys Ser Phe Thr Thr Leu Pro Ala Leu Ser Thr Gly
                675                 680                 685
Leu Ile His Leu His Gln Asn Ile Val Asp Val Gln Tyr Leu Tyr Gly
            690                 695                 700
Val Gly Ser Ser Val Val Ser Ile Ala Ile Arg Trp Glu Tyr Val Val
705                 710                 715                 720
Leu Leu Phe Leu Leu Leu Ala Asp Ala Arg Val Cys Ala Cys Leu Trp
                725                 730                 735
Met Met Leu Leu Ile Ala Gln Ala Glu Ala Ala Leu Glu Asn Leu Val
            740                 745                 750
```

```
Ile Leu Asn Ala Ala Ser Val Ala Gly Ala His Gly Val Leu Ser Phe
        755                 760                 765

Leu Val Phe Phe Cys Ala Ala Trp Tyr Ile Lys Gly Lys Leu Val Pro
770                 775                 780

Gly Ala Ala Tyr Ala Phe Tyr Gly Val Trp Pro Leu Leu Leu Leu Leu
785                 790                 795                 800

Leu Ser Leu Pro Pro Arg Ala Tyr Ala Leu Asp Arg Glu Met Ala Ala
                805                 810                 815

Ser Cys Gly Gly Ala Val Phe Val Gly Leu Met Leu Thr Leu Ser
                820                 825                 830

Pro His Tyr Lys Val Phe Leu Ala Arg Leu Ile Trp Trp Leu Gln Tyr
            835                 840                 845

Phe Ile Thr Arg Ala Glu Ala His Leu Gln Val Trp Val Pro Pro Leu
850                 855                 860

Asn Val Arg Gly Gly Arg Asp Ala Ile Ile Leu Leu Thr Cys Val Val
865                 870                 875                 880

His Pro Glu Leu Ile Phe Asp Ile Thr Lys Ile Leu Leu Ala Met Leu
                885                 890                 895

Gly Pro Leu Met Val Leu Gln Ala Gly Leu Thr Arg Val Pro Tyr Phe
            900                 905                 910

Val Arg Ala Gln Gly Leu Ile Arg Ala Cys Met Leu Val Arg Lys Val
            915                 920                 925

Ala Gly Gly His Tyr Val Gln Met Ala Leu Met Lys Leu Ala Ala Leu
        930                 935                 940

Thr Gly Thr Tyr Val Tyr Asp His Leu Thr Pro Leu Gln Asp Trp Ala
945                 950                 955                 960

His Ala Gly Leu Arg Asp Leu Ala Val Ala Val Glu Pro Val Val Phe
                965                 970                 975

Ser Asp Thr Glu Thr Lys Val Ile Thr Trp Gly Ala Asp Thr Ala Ala
            980                 985                 990

Cys Gly Asp Ile Ile Ser Gly Leu Pro Val Ser Ala Arg Arg Gly Arg
        995                 1000                1005

Glu Ile Leu Leu Gly Pro Ala Asp Arg Phe Gly Glu Gln Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Val Gln Val Val Ser Thr Ala Thr Gln Ser
    1055                1060                1065

Phe Leu Ala Thr Cys Val Asn Gly Val Cys Trp Thr Val Tyr His
    1070                1075                1080

Gly Ala Gly Ser Lys Thr Leu Ala Gly Pro Lys Gly Pro Ile Thr
    1085                1090                1095

Gln Met Tyr Thr Asn Val Asp Gln Asp Leu Val Gly Trp Pro Ala
    1100                1105                1110

Pro Pro Gly Ala Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Ile
    1145                1150                1155
```

```
Ser Tyr Leu Lys Gly Ser Ser Gly Gly Pro Leu Leu Cys Pro Leu
1160                1165                1170

Gly His Ala Val Gly Ile Phe Arg Ala Ala Val Cys Thr Arg Gly
1175                1180                1185

Val Ala Lys Ala Val Asp Phe Val Pro Val Glu Ser Met Glu Thr
1190                1195                1200

Thr Met Arg Ser Pro Val Phe Thr Asp Asn Ser Ser Pro Pro Ala
1205                1210                1215

Val Pro Gln Thr Phe Gln Val Ala His Leu His Ala Pro Thr Gly
1220                1225                1230

Ser Gly Lys Ser Thr Lys Val Pro Ala Ala Tyr Ala Ala Gln Gly
1235                1240                1245

Tyr Lys Val Leu Val Leu Asn Pro Ser Val Ala Ala Thr Leu Gly
1250                1255                1260

Phe Gly Ala Tyr Met Ser Lys Ala His Gly Val Glu Pro Asn Ile
1265                1270                1275

Arg Thr Gly Val Arg Thr Ile Thr Thr Gly Ala Ser Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys His Ser Thr Asp Ser
1310                1315                1320

Thr Ser Ile Leu Gly Ile Gly Thr Val Leu Asp Gln Ala Glu Thr
1325                1330                1335

Ala Gly Ala Arg Leu Val Val Leu Ala Thr Ala Thr Pro Pro Gly
1340                1345                1350

Ser Val Thr Val Pro His Pro Asn Ile Glu Glu Val Ala Leu Pro
1355                1360                1365

Ser Thr Gly Glu Ile Pro Phe Tyr Gly Lys Ala Ile Pro Ile Glu
1370                1375                1380

Thr Ile Lys Gly Gly Arg His Leu Ile Phe Cys His Ser Lys Lys
1385                1390                1395

Lys Cys Asp Glu Leu Ala Ala Lys Leu Val Gly Leu Gly Val Asn
1400                1405                1410

Ala Val Ala Tyr Tyr Arg Gly Leu Asp Val Ser Val Ile Pro Thr
1415                1420                1425

Ser Gly Asp Val Val Val Val Ala Thr Asp Ala Leu Met Thr Gly
1430                1435                1440

Phe Thr Gly Asp Phe Asp Ser Val Ile Asp Cys Asn Thr Cys Val
1445                1450                1455

Thr Gln Thr Val Asp Phe Ser Leu Asp Pro Thr Phe Thr Ile Glu
1460                1465                1470

Thr Thr Thr Val Pro Gln Asp Ala Val Ser Arg Ser Gln Arg Arg
1475                1480                1485

Gly Arg Thr Gly Arg Gly Arg Met Gly Ile Tyr Arg Phe Val Ala
1490                1495                1500

Pro Gly Glu Arg Pro Ser Gly Met Phe Asp Ser Ser Val Leu Cys
1505                1510                1515

Glu Cys Tyr Asp Ala Gly Cys Ala Trp Tyr Glu Leu Thr Pro Ala
1520                1525                1530

Glu Thr Ser Val Arg Leu Arg Ala Tyr Leu Asn Thr Pro Gly Leu
1535                1540                1545

Pro Val Cys Gln Asp His Leu Glu Phe Trp Glu Gly Val Phe Thr
```

```
                    1550                   1555                   1560
Gly Leu Thr His Ile Asp Ala His Phe Leu Ser Gln Thr Lys Gln
    1565                   1570                   1575

Ala Gly Asp Asn Phe Pro Tyr Leu Val Ala Tyr Gln Ala Thr Val
    1580                   1585                   1590

Cys Ala Arg Ala Gln Ala Pro Pro Ser Trp Asp Gln Met Trp
    1595                   1600                   1605

Lys Cys Leu Ile Arg Leu Lys Pro Thr Leu His Gly Pro Thr Pro
    1610                   1615                   1620

Leu Leu Tyr Arg Leu Gly Ala Val Gln Asn Glu Val Ile Leu Thr
    1625                   1630                   1635

His Pro Ile Thr Lys Tyr Ile Met Ala Cys Met Ser Ala Asp Leu
    1640                   1645                   1650

Glu Val Val Thr Ser Thr Trp Val Leu Val Gly Gly Val Leu Ala
    1655                   1660                   1665

Ala Leu Ala Ala Tyr Cys Leu Thr Thr Gly Ser Val Val Ile Val
    1670                   1675                   1680

Gly Arg Ile Ile Leu Ser Gly Lys Pro Ala Ile Ile Pro Asp Arg
    1685                   1690                   1695

Glu Val Leu Tyr Arg Glu Phe Asp Glu Met Glu Glu Cys Ala Ser
    1700                   1705                   1710

His Leu Pro Tyr Ile Glu Gln Gly Met Gln Leu Ala Glu Gln Phe
    1715                   1720                   1725

Lys Gln Lys Ala Leu Gly Leu Leu Gln Thr Ala Thr Lys Gln Ala
    1730                   1735                   1740

Glu Ala Ala Ala Pro Val Val Glu Ser Lys Trp Arg Ala Leu Glu
    1745                   1750                   1755

Ala Phe Trp Ala Lys His Met Trp Asn Phe Ile Ser Gly Ile Gln
    1760                   1765                   1770

Tyr Leu Ala Gly Leu Ser Thr Leu Pro Gly Asn Pro Ala Ile Ala
    1775                   1780                   1785

Ser Leu Met Ala Phe Thr Ala Ser Ile Thr Ser Pro Leu Thr Thr
    1790                   1795                   1800

Leu His Thr Leu Leu Phe Asn Ile Leu Gly Gly Trp Val Ala Ala
    1805                   1810                   1815

Gln Leu Ala Pro Pro Gly Ala Ala Ser Ala Phe Val Gly Ala Gly
    1820                   1825                   1830

Ile Ala Gly Ala Ala Val Gly Ser Ile Gly Leu Gly Lys Val Leu
    1835                   1840                   1845

Val Asp Ile Leu Ala Gly Tyr Gly Ala Gly Val Ala Gly Ala Leu
    1850                   1855                   1860

Val Ala Phe Lys Val Met Ser Gly Glu Met Pro Ser Thr Glu Asp
    1865                   1870                   1875

Leu Val Asn Leu Leu Pro Ala Ile Leu Ser Pro Gly Ala Leu Val
    1880                   1885                   1890

Val Gly Val Val Cys Ala Ala Ile Leu Arg Arg His Val Gly Pro
    1895                   1900                   1905

Gly Glu Gly Ala Val Gln Trp Met Asn Arg Leu Ile Ala Phe Ala
    1910                   1915                   1920

Ser Arg Gly Asn His Val Ser Pro Thr His Tyr Val Pro Glu Ser
    1925                   1930                   1935

Asp Ala Ala Ala Arg Val Thr Gln Ile Leu Ser Ser Leu Thr Ile
    1940                   1945                   1950
```

```
Thr Gln Leu Leu Lys Arg Leu His Gln Trp Ile Asn Lys Asp Cys
    1955            1960            1965

Ser Thr Pro Cys Ser Gly Ser Trp Leu Arg Asp Val Trp Asp Trp
    1970            1975            1980

Ile Cys Thr Val Leu Ser Asp Phe Lys Thr Trp Leu Gln Ser Lys
    1985            1990            1995

Leu Leu Pro Arg Leu Pro Gly Val Pro Phe Leu Ser Cys Gln Arg
    2000            2005            2010

Gly Tyr Lys Gly Val Trp Arg Gly Asp Gly Ile Met Gln Thr Ser
    2015            2020            2025

Cys Pro Cys Gly Ala Gln Ile Ala Gly His Val Lys Asn Gly Ser
    2030            2035            2040

Met Arg Ile Val Gly Pro Lys Thr Cys Ser Asn Thr Trp His Gly
    2045            2050            2055

Thr Phe Pro Ile Asn Ala His Thr Thr Gly Pro Cys Thr Pro Ser
    2060            2065            2070

Pro Ala Pro Asn Tyr Ser Lys Ala Leu Trp Arg Val Ala Ala Glu
    2075            2080            2085

Glu Tyr Val Glu Val Thr Arg Val Gly Asp Phe His Tyr Val Thr
    2090            2095            2100

Gly Met Thr Thr Asp Asn Val Lys Cys Pro Cys Gln Val Pro Ala
    2105            2110            2115

Pro Glu Phe Phe Thr Glu Val Asp Gly Val Arg Leu His Arg Tyr
    2120            2125            2130

Ala Pro Ala Cys Lys Pro Leu Leu Arg Asp Glu Val Thr Phe Gln
    2135            2140            2145

Val Gly Leu Asn Gln Phe Pro Val Gly Ser Gln Leu Pro Cys Glu
    2150            2155            2160

Pro Glu Pro Asp Val Ser Val Leu Thr Ser Met Leu Thr Asp Pro
    2165            2170            2175

Ser His Ile Thr Ala Glu Thr Ala Lys Arg Arg Leu Ala Arg Gly
    2180            2185            2190

Ser Ser Pro Ser Leu Ala Ser Ser Ser Ala Ser Gln Leu Ser Ala
    2195            2200            2205

Pro Ser Leu Lys Ala Thr Cys Thr Thr His His Asp Ser Pro Asp
    2210            2215            2220

Ala Asp Leu Ile Glu Ala Asn Leu Leu Trp Arg Gln Glu Met Gly
    2225            2230            2235

Gly Asn Ile Thr Arg Val Glu Ser Glu Asn Lys Val Val Ile Leu
    2240            2245            2250

Asp Ser Phe Asp Pro Leu Arg Ala Glu Glu Asp Glu Arg Glu Val
    2255            2260            2265

Ser Val Ala Ala Glu Ile Leu Arg Lys Thr Arg Lys Phe Pro Pro
    2270            2275            2280

Ala Met Pro Ile Trp Ala Arg Pro Asp Tyr Asn Pro Pro Leu Leu
    2285            2290            2295

Glu Thr Trp Lys Asp Pro Asp Tyr Val Pro Pro Val Val His Gly
    2300            2305            2310

Cys Pro Leu Pro Pro Thr Lys Thr Pro Pro Ile Pro Pro Pro Arg
    2315            2320            2325

Arg Lys Lys Thr Val Val Leu Thr Glu Ser Thr Val Ser Ser Ala
    2330            2335            2340
```

-continued

| | | | | | | | | | | |
|---|---|---|---|---|---|---|---|---|---|---|
|Leu|Ala|Glu|Leu|Ala|Thr|Lys|Thr|Phe|Gly|Ser|Ser|Gly|Ser|Ser|
|2345| | | | |2350| | | | |2355| | | | |

Ala Val Asp Ser Gly Thr Ala Thr Ala Pro Pro Asn Gln Leu Ser
2360 2365 2370

Asp Glu Val Asp Thr Gly Ser Asp Val Glu Ser Tyr Ser Ser Met
2375 2380 2385

Pro Pro Leu Glu Gly Glu Pro Gly Asp Pro Asp Leu Ser Asp Gly
2390 2395 2400

Ser Trp Ser Thr Val Ser Glu Glu Ala Gly Glu Asp Val Val Cys
2405 2410 2415

Cys Ser Met Ser Tyr Thr Trp Thr Gly Ala Leu Ile Thr Pro Cys
2420 2425 2430

Ala Ala Glu Glu Ser Lys Leu Pro Ile Asn Ala Leu Ser Asn Ser
2435 2440 2445

Leu Leu Arg His His Asn Met Val Tyr Ala Thr Thr Ser Arg Ser
2450 2455 2460

Ala Ser Gln Arg Gln Lys Lys Val Thr Phe Asp Arg Leu Gln Val
2465 2470 2475

Leu Asp Asp His Tyr Arg Asp Val Leu Lys Glu Met Lys Ala Lys
2480 2485 2490

Ala Ser Thr Val Lys Ala Lys Leu Leu Ser Val Glu Glu Ala Cys
2495 2500 2505

Lys Leu Thr Pro Pro His Ser Ala Arg Ser Lys Phe Gly Tyr Gly
2510 2515 2520

Ala Lys Asp Val Arg Asn Leu Ser Ser Lys Ala Val Asn His Ile
2525 2530 2535

Asn Ser Val Trp Lys Asp Leu Leu Glu Asp Thr Glu Thr Pro Ile
2540 2545 2550

Asp Thr Thr Ile Met Ala Lys Asn Glu Val Phe Cys Val Gln Pro
2555 2560 2565

Glu Lys Gly Gly Arg Lys Pro Ala Arg Leu Ile Val Tyr Pro Asp
2570 2575 2580

Leu Gly Val Arg Val Cys Glu Lys Met Ala Leu Tyr Asp Val Val
2585 2590 2595

Ser Thr Leu Pro Gln Ala Val Met Gly Ser Ser Tyr Gly Phe Gln
2600 2605 2610

Tyr Ser Pro Gly Gln Arg Val Glu Phe Leu Val Asn Ala Trp Lys
2615 2620 2625

Ser Lys Lys Asn Pro Met Gly Phe Ala Tyr Asp Thr Arg Cys Phe
2630 2635 2640

Asp Ser Thr Val Thr Glu Asn Asp Ile Arg Val Glu Glu Ser Ile
2645 2650 2655

Tyr Gln Cys Cys Asp Leu Ala Pro Glu Ala Arg Gln Val Ile Arg
2660 2665 2670

Ser Leu Thr Glu Arg Leu Tyr Val Gly Gly Pro Leu Thr Asn Ser
2675 2680 2685

Lys Gly Gln Asn Cys Gly Tyr Arg Arg Cys Arg Ala Ser Gly Val
2690 2695 2700

Leu Thr Thr Ser Cys Gly Asn Thr Leu Thr Cys Tyr Leu Lys Ala
2705 2710 2715

Ser Ala Ala Cys Arg Ala Ala Lys Leu Gln Asp Cys Thr Met Leu
2720 2725 2730

Val Cys Gly Asp Asp Leu Val Val Ile Cys Glu Ser Ala Gly Thr

```
                 2735                2740                2745

Gln  Glu  Asp  Ala  Ala  Ser  Leu  Arg  Val  Phe  Thr  Glu  Ala  Met  Thr
          2750                2755                2760

Arg  Tyr  Ser  Ala  Pro  Pro  Gly  Asp  Pro  Pro  Arg  Pro  Glu  Tyr  Asp
          2765                2770                2775

Leu  Glu  Leu  Ile  Thr  Ser  Cys  Ser  Ser  Asn  Val  Ser  Val  Ala  His
          2780                2785                2790

Asp  Ala  Ser  Gly  Lys  Arg  Val  Tyr  Tyr  Leu  Thr  Arg  Asp  Pro  Thr
          2795                2800                2805

Thr  Pro  Leu  Ala  Arg  Ala  Ala  Trp  Glu  Thr  Ala  Lys  His  Thr  Pro
          2810                2815                2820

Val  Asn  Ser  Trp  Leu  Gly  Asn  Ile  Ile  Met  Tyr  Ala  Pro  Thr  Leu
          2825                2830                2835

Trp  Ala  Arg  Met  Ile  Leu  Met  Thr  His  Phe  Phe  Ser  Ile  Leu  Leu
          2840                2845                2850

Ala  Gln  Glu  Gln  Leu  Glu  Lys  Ala  Leu  Asp  Cys  Gln  Ile  Tyr  Gly
          2855                2860                2865

Ala  Thr  Tyr  Ser  Ile  Glu  Pro  Leu  Asp  Leu  Pro  Gln  Ile  Ile  Gln
          2870                2875                2880

Arg  Leu  His  Gly  Leu  Ser  Ala  Phe  Ser  Leu  His  Ser  Tyr  Ser  Pro
          2885                2890                2895

Gly  Glu  Ile  Asn  Arg  Val  Ala  Ser  Cys  Leu  Arg  Lys  Leu  Gly  Val
          2900                2905                2910

Pro  Pro  Leu  Arg  Val  Trp  Arg  His  Arg  Ala  Arg  Ser  Val  Arg  Ala
          2915                2920                2925

Lys  Leu  Leu  Ser  Gln  Gly  Gly  Arg  Ala  Ala  Thr  Cys  Gly  Lys  Tyr
          2930                2935                2940

Leu  Phe  Asn  Trp  Ala  Val  Arg  Thr  Lys  Leu  Lys  Leu  Thr  Pro  Ile
          2945                2950                2955

Pro  Ala  Ala  Ser  Gln  Leu  Asp  Leu  Ser  Gly  Trp  Phe  Ile  Ala  Gly
          2960                2965                2970

Tyr  Ser  Gly  Gly  Asp  Ile  Tyr  His  Ser  Leu  Ser  Arg  Ala  Arg  Pro
          2975                2980                2985

Arg  Trp  Phe  Met  Leu  Cys  Leu  Leu  Leu  Leu  Ser  Val  Gly  Val  Gly
          2990                2995                3000

Ile  Tyr  Leu  Leu  Pro  Asn  Arg
          3005                3010

<210> SEQ ID NO 3
<211> LENGTH: 651
<212> TYPE: DNA
<213> ORGANISM: Hepatitis C virus
<220> FEATURE:
<221> NAME/KEY: CDS
<222> LOCATION: (1)..(651)
<223> OTHER INFORMATION:

<400> SEQUENCE: 3 ttg  gac  cgg  gag  atg  gct  gca  tcg  tgc  gga  ggc  gcg  gtt  ttc  gta  ggt        48
Leu  Asp  Arg  Glu  Met  Ala  Ala  Ser  Cys  Gly  Gly  Ala  Val  Phe  Val  Gly
1                 5                   10                  15 ctg  atg  ctc  ctg  acc  ttg  tca  cca  cac  tac  aag  gtg  ttt  ctc  gct  agg        96
Leu  Met  Leu  Leu  Thr  Leu  Ser  Pro  His  Tyr  Lys  Val  Phe  Leu  Ala  Arg
                  20                  25                  30 ctc  ata  tgg  tgg  tta  cag  tat  ttt  atc  acc  agg  gcc  gag  gcg  cac  ttg        144
Leu  Ile  Trp  Trp  Leu  Gln  Tyr  Phe  Ile  Thr  Arg  Ala  Glu  Ala  His  Leu
                  35                  40                  45
```

```
cag gtg tgg gtc ccc ccc ctc aac gtt cgg ggg ggc cgc gat gcc atc    192
Gln Val Trp Val Pro Pro Leu Asn Val Arg Gly Gly Arg Asp Ala Ile
    50              55                  60 atc ctc ctc acg tgt gtg gtc cac cca gag cta att ttt gac atc acc    240
Ile Leu Leu Thr Cys Val Val His Pro Glu Leu Ile Phe Asp Ile Thr
65              70                  75                  80 aaa atc ttg ctc gcc atg ctc ggt ccg ctc atg gtg ctc cag gct ggc    288
Lys Ile Leu Leu Ala Met Leu Gly Pro Leu Met Val Leu Gln Ala Gly
                85                  90                  95 cta act aga gtg ccg tac ttc gta cgc gct caa ggg ctc atc cgt gca    336
Leu Thr Arg Val Pro Tyr Phe Val Arg Ala Gln Gly Leu Ile Arg Ala
            100                 105                 110 tgc atg tta gtg cgg aaa gtc gct ggg ggc cac tat gtc caa atg gcc    384
Cys Met Leu Val Arg Lys Val Ala Gly Gly His Tyr Val Gln Met Ala
        115                 120                 125 ctc atg aaa ctg gcc gca ctg acg ggt acg tac gtt tat gac cat ctt    432
Leu Met Lys Leu Ala Ala Leu Thr Gly Thr Tyr Val Tyr Asp His Leu
    130                 135                 140 act ccg ctg cag gac tgg gcc cac gcg ggc ttg cga gac ctt gca gtg    480
Thr Pro Leu Gln Asp Trp Ala His Ala Gly Leu Arg Asp Leu Ala Val
145                 150                 155                 160 gca gtt gag ccc gtc gtc ttc tct gac acg gag act aag gtc atc acc    528
Ala Val Glu Pro Val Val Phe Ser Asp Thr Glu Thr Lys Val Ile Thr
                165                 170                 175 tgg ggg gca gac acc gca gcg tgt ggg gac atc atc tcg ggc cta ccc    576
Trp Gly Ala Asp Thr Ala Ala Cys Gly Asp Ile Ile Ser Gly Leu Pro
            180                 185                 190 gtc tcc gcc cga agg ggg agg gag ata ctt ctg ggc ccc gcc gac agg    624
Val Ser Ala Arg Arg Gly Arg Glu Ile Leu Leu Gly Pro Ala Asp Arg
        195                 200                 205 ttt gga gag cag ggg tgg cga ctc ctc                                651
Phe Gly Glu Gln Gly Trp Arg Leu Leu
    210                 215
```

<210> SEQ ID NO 4
<211> LENGTH: 217
<212> TYPE: PRT
<213> ORGANISM: Hepatitis C virus

<400> SEQUENCE: 4

```
Leu Asp Arg Glu Met Ala Ala Ser Cys Gly Gly Ala Val Phe Val Gly
1               5                   10                  15

Leu Met Leu Leu Thr Leu Ser Pro His Tyr Lys Val Phe Leu Ala Arg
            20                  25                  30

Leu Ile Trp Trp Leu Gln Tyr Phe Ile Thr Arg Ala Glu Ala His Leu
        35                  40                  45

Gln Val Trp Val Pro Pro Leu Asn Val Arg Gly Gly Arg Asp Ala Ile
    50                  55                  60

Ile Leu Leu Thr Cys Val Val His Pro Glu Leu Ile Phe Asp Ile Thr
65              70                  75                  80

Lys Ile Leu Leu Ala Met Leu Gly Pro Leu Met Val Leu Gln Ala Gly
                85                  90                  95

Leu Thr Arg Val Pro Tyr Phe Val Arg Ala Gln Gly Leu Ile Arg Ala
            100                 105                 110

Cys Met Leu Val Arg Lys Val Ala Gly Gly His Tyr Val Gln Met Ala
        115                 120                 125

Leu Met Lys Leu Ala Ala Leu Thr Gly Thr Tyr Val Tyr Asp His Leu
    130                 135                 140
```

```
Thr Pro Leu Gln Asp Trp Ala His Ala Gly Leu Arg Asp Leu Ala Val
145                 150                 155                 160

Ala Val Glu Pro Val Val Phe Ser Asp Thr Glu Thr Lys Val Ile Thr
                165                 170                 175

Trp Gly Ala Asp Thr Ala Ala Cys Gly Asp Ile Ile Ser Gly Leu Pro
            180                 185                 190

Val Ser Ala Arg Arg Gly Arg Glu Ile Leu Leu Gly Pro Ala Asp Arg
        195                 200                 205

Phe Gly Glu Gln Gly Trp Arg Leu Leu
    210                 215

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
tcatgcggct cacggacctt tcacagctag                                      30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
atcgtcttca cgcagaaagc gtctagccat                                      30

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gcctattggc ctggagtgtt tagctc                                          26

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
atggcgttag tatgagtgtc gtgcagcct                                       29

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
tcgggcacga gacaggctgt gatatatgtc t                                    31

<210> SEQ ID NO 10
<211> LENGTH: 19
```

<212> TYPE: DNA
<213> ORGANISM: Artificial Sequence
<220> FEATURE:
<223> OTHER INFORMATION: Primer

<400> SEQUENCE: 10
tgcacggtct acgagacct                                                         19

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ctcgcaagca ccctatcagc cagt                                                   24

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
aggcattgag cgggtttat                                                         19

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
ctagactcga gtcgacatcg tttttttttt tttttttt                                    38

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
atcttagccc tagtcacggc                                                        20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ctagactcga gtcgacatcg                                                        20

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
ctagctgtaa aggtccgtga gccgcatga                                              29

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17
gtaaaacgac ggccagt                                                           17

<210> SEQ ID NO 18
<211> LENGTH: 17
<212> TYPE: DNA
<213> ORGANISM: Artificial Sequence
<220> FEATURE:
<223> OTHER INFORMATION: Primer

<400> SEQUENCE: 18
caggaaacag ctatgac                                                           17

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aggaagactt ccgagcggtc                                                        20

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
ggaacttgcc cggttgctct ttctctatct tc                                          32

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
attccatggt ggggaactgg gctaa                                                  25

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
taacaatacc ttgacctgcc ccacggactg                                             30

<210> SEQ ID NO 23
<211> LENGTH: 29
<212> TYPE: DNA
<213> ORGANISM: Artificial Sequence

```
<220> FEATURE:
<223> OTHER INFORMATION: Primer

<400> SEQUENCE: 23
aacatcgtgg acgtgcaata cctgtacgg                                   29

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gaccctacac cgtacaggta                                             20

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
ttggaccggg agatggctgc atcgtg                                      26

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
cacccaaatg tacaccaatg t                                           21

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tacccgttga gtctatggaa ac                                          22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cacttggaat gtctgcggta                                             20

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
agggggggag gcatctcatt ttctg                                       25
```

```
<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
tgctatgacg cgggctgtgc ttggta                                          26

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ggtcattgtg ggcaggatca t                                               21

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ctgcctggaa accccgcgat                                                 20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
tggcagcata ggccttggga aggt                                            24

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
aagacctggc tccagtccaa g                                               21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
ttccatgctc accgacccct c                                               21

<210> SEQ ID NO 36
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 36
gtggagtcag agaataaggt                                                    20

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
cagaagaagg tcacctttga c                                                  21

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
gcagcgggtc gagttcctgg tgaat                                              25

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
ctacggggcc tgttactcca ttgaac                                             26

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
accggtgagt acaccggaat tgccaggacg                                         30

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
atttgggtga ttgggccctt cgggccggcc                                         30
```